(12) United States Patent
Ding et al.

(10) Patent No.: US 10,624,843 B2
(45) Date of Patent: Apr. 21, 2020

(54) MICROSTRUCTURE ARRAY, METHODS OF MAKING, AND METHODS OF USE

(71) Applicant: Corium International, Inc., Menlo Park, CA (US)

(72) Inventors: Zhongli Ding, Sunnyvale, CA (US); Guohua Chen, Sunnyvale, CA (US); Parminder Singh, Union City, CA (US)

(73) Assignee: Corium, Inc., Menlo Park, CA (US)

( * ) Notice: Subject to any disclaimer, the term of this patent is extended or adjusted under 35 U.S.C. 154(b) by 372 days.

(21) Appl. No.: 14/843,914

(22) Filed: Sep. 2, 2015

(65) Prior Publication Data
US 2016/0067176 A1 Mar. 10, 2016

Related U.S. Application Data

(60) Provisional application No. 62/046,098, filed on Sep. 4, 2014.

(51) Int. Cl.
| | | |
|---|---|---|
| *A61K 47/22* | (2006.01) | |
| *A61K 47/32* | (2006.01) | |
| *A61K 47/36* | (2006.01) | |
| *A61K 47/44* | (2017.01) | |
| *A61K 9/00* | (2006.01) | |
| *A61M 37/00* | (2006.01) | |
| *A61K 47/42* | (2017.01) | |

(52) U.S. Cl.
CPC ........ *A61K 9/0021* (2013.01); *A61M 37/0015* (2013.01); *A61K 47/22* (2013.01); *A61K 47/32* (2013.01); *A61K 47/36* (2013.01); *A61K 47/42* (2013.01); *A61M 2037/0023* (2013.01); *A61M 2037/0053* (2013.01)

(58) Field of Classification Search
CPC ........ A61M 2205/0244; A61M 31/002; A61M 37/0015; A61M 2037/0023; A61M 2037/0053; A61K 9/0097; A61K 9/0021
See application file for complete search history.

(56) References Cited

U.S. PATENT DOCUMENTS

| | | | |
|---|---|---|---|
| 1,554,510 | A | 9/1925 | Kirby |
| 1,770,632 | A | 7/1930 | Smith |
| 2,046,240 | A | 6/1936 | Bayley |

(Continued)

FOREIGN PATENT DOCUMENTS

| | | |
|---|---|---|
| CA | 2205444 | 6/1996 |
| CA | 2376285 | 12/2000 |

(Continued)

OTHER PUBLICATIONS

Avcin et al., "Subcutaneous nodule after vaccination with an aluminum-containing vaccina", Acta Dermatoven, APA, vol. 17, No. 4, pp. 182-184 (2008).

(Continued)

*Primary Examiner* — Bhisma Mehta
*Assistant Examiner* — William R Frehe
(74) *Attorney, Agent, or Firm* — McDermott Will & Emery LLP; Judy M. Mohr; Edward J. DesJardins

(57) ABSTRACT

A microprojection array comprising an approximately planar base and a plurality of microprojections, wherein the array comprises a therapeutic agent that is poorly soluble in water or an aqueous solvent.

12 Claims, 5 Drawing Sheets

(56) References Cited

U.S. PATENT DOCUMENTS

| | | |
|---|---|---|
| 2,434,407 A | 1/1948 | George |
| 3,675,766 A | 7/1972 | Rosenthal |
| 3,704,194 A | 11/1972 | Harrier et al. |
| 3,814,097 A | 6/1974 | Ganderton et al. |
| 3,873,255 A | 3/1975 | Kalwaites |
| 3,918,449 A | 11/1975 | Pistor |
| 3,964,482 A | 6/1976 | Gerstel et al. |
| 4,055,029 A | 10/1977 | Kalbow |
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,660,721 A | 4/1987 | Mykleby |
| 4,695,422 A | 9/1987 | Curro et al. |
| 4,743,234 A | 5/1988 | Leopoldi et al. |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,996,159 A | 2/1991 | Glaser |
| 5,051,259 A | 9/1991 | Olsen et al. |
| 5,061,258 A | 10/1991 | Martz |
| 5,134,079 A | 7/1992 | Cusack et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,163,918 A | 11/1992 | Righi et al. |
| 5,190,558 A | 3/1993 | Ito |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabenau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,287 A | 6/1996 | Miskinyar |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,569,469 A | 10/1996 | Lovrechich |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Eriksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,868,244 A | 2/1999 | Ivanov et al. |
| 5,873,849 A | 2/1999 | Bernard |
| 5,879,326 A | 3/1999 | Godshall et al. |
| 5,900,252 A | 5/1999 | Calanchi et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |
| 6,055,453 A | 4/2000 | Hofmann et al. |
| 6,080,172 A | 6/2000 | Fujiwara et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,248,120 B1 | 6/2001 | Wyszogrodzki |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |

(56) References Cited

U.S. PATENT DOCUMENTS

| | | |
|---|---|---|
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kleiner et al. |
| 6,379,324 B1 | 4/2002 | Garstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,476,288 B1 | 11/2002 | Van Rijswijck et al. |
| 6,485,470 B2 | 11/2002 | Hostettler et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,512,626 B1 | 1/2003 | Schmidt |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whitson |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 6,991,809 B2 | 1/2006 | Anderson |
| 7,011,844 B2 | 3/2006 | Gale et al. |
| 7,048,723 B1 * | 5/2006 | Frazier .............. A61M 37/0015 604/272 |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,128,730 B2 | 10/2006 | Marano-Ford et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,419,481 B2 | 9/2008 | Trautman et al. |
| 7,572,405 B2 | 8/2009 | Sherman et al. |
| 7,578,954 B2 | 8/2009 | Gartstein et al. |
| 7,578,985 B2 | 8/2009 | Aderhold et al. |
| 7,611,481 B2 | 11/2009 | Cleary et al. |
| 7,658,728 B2 | 2/2010 | Yuzhakov |
| 7,678,777 B2 | 3/2010 | Yasuda et al. |
| 7,763,203 B2 | 7/2010 | Arias et al. |
| 7,785,301 B2 | 8/2010 | Yuzhakov |
| 7,789,733 B2 | 9/2010 | Sugimura |
| 7,798,987 B2 | 9/2010 | Trautman et al. |
| 7,828,827 B2 | 11/2010 | Gartstein et al. |
| 7,846,488 B2 | 12/2010 | Johnson |
| 7,914,480 B2 | 3/2011 | Cleary et al. |
| 8,057,842 B2 | 11/2011 | Choi et al. |
| 8,062,573 B2 | 11/2011 | Kwon |
| 8,216,190 B2 | 7/2012 | Gartstein et al. |
| 8,267,889 B2 | 9/2012 | Cantor et al. |
| 8,366,677 B2 | 2/2013 | Kaspar et al. |
| 8,696,638 B2 | 4/2014 | Terahara et al. |
| 8,702,726 B2 | 4/2014 | Gartstein et al. |
| 8,734,697 B2 | 5/2014 | Chen et al. |
| 8,747,362 B2 | 6/2014 | Terahara |
| 8,771,781 B2 | 7/2014 | Tokumoto et al. |
| 8,821,446 B2 | 9/2014 | Trautman et al. |
| 8,834,423 B2 | 9/2014 | Falo, Jr. et al. |
| 8,900,180 B2 | 12/2014 | Wolter et al. |
| 8,911,749 B2 | 12/2014 | Ghartey-Tagoe et al. |
| 9,114,238 B2 | 8/2015 | Singh et al. |
| 9,220,678 B2 | 12/2015 | Kendall et al. |
| 9,452,280 B2 | 9/2016 | Singh et al. |
| 9,498,524 B2 | 11/2016 | Ghartey-Tagoe et al. |
| 9,549,746 B2 | 1/2017 | Woolfsen et al. |
| 9,687,640 B2 | 6/2017 | Trautman et al. |
| 9,687,641 B2 | 6/2017 | Singh et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0123675 A1 | 9/2002 | Trautman et al. |
| 2002/0128599 A1 | 9/2002 | Cormier et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0188310 A1 | 12/2002 | Seward et al. |
| 2002/0193729 A1 | 12/2002 | Cormier et al. |
| 2002/0193819 A1 | 12/2002 | Porter et al. |
| 2003/0083645 A1 | 5/2003 | Angel et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0049150 A1 | 3/2004 | Dalton et al. |
| 2004/0053894 A1 * | 3/2004 | Mazess ............... A61K 9/0019 514/167 |
| 2004/0062813 A1 | 4/2004 | Cormier et al. |
| 2004/0087893 A1 | 5/2004 | Kwon |
| 2004/0087992 A1 | 5/2004 | Gartstein et al. |
| 2004/0096455 A1 | 5/2004 | Maa et al. |

(56) References Cited

U.S. PATENT DOCUMENTS

| | | |
|---|---|---|
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1 | 3/2005 | Wong et al. |
| 2005/0065463 A1 | 3/2005 | Tobinga et al. |
| 2005/0089554 A1 | 4/2005 | Cormier et al. |
| 2005/0090803 A1 | 4/2005 | Sherman et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2005/0256045 A1 | 11/2005 | Ameri et al. |
| 2005/0261631 A1 | 11/2005 | Clarke et al. |
| 2005/0271684 A1 | 12/2005 | Trautman et al. |
| 2006/0024358 A1 | 2/2006 | Santini et al. |
| 2006/0067943 A1 | 3/2006 | Maa et al. |
| 2006/0076718 A1 | 4/2006 | Sherman et al. |
| 2006/0095061 A1 | 5/2006 | Trautman et al. |
| 2006/0108914 A1 | 5/2006 | Young |
| 2006/0129174 A1 | 6/2006 | Gartstein et al. |
| 2006/0134188 A1 | 6/2006 | Podhaisky et al. |
| 2006/0149297 A1 | 7/2006 | Sherman et al. |
| 2006/0253079 A1 | 11/2006 | McDonough et al. |
| 2007/0027427 A1 | 2/2007 | Trautman et al. |
| 2007/0191761 A1 | 8/2007 | Boone et al. |
| 2007/0255251 A1 | 11/2007 | Panchula et al. |
| 2008/0009811 A1 | 1/2008 | Cantor |
| 2008/0009825 A1 | 1/2008 | Ringsred et al. |
| 2008/0039805 A1 | 2/2008 | Frederickson et al. |
| 2008/0114298 A1 | 5/2008 | Cantor et al. |
| 2008/0125743 A1 | 5/2008 | Yuzhakov |
| 2008/0183144 A1 | 7/2008 | Trautman et al. |
| 2008/0188771 A1 | 8/2008 | Boecker et al. |
| 2008/0195035 A1 | 8/2008 | Frederickson et al. |
| 2008/0208134 A1 | 8/2008 | Tomono |
| 2008/0208146 A1 | 8/2008 | Brandwein et al. |
| 2008/0214987 A1 | 9/2008 | Xu |
| 2008/0221532 A1 | 9/2008 | Ogawa |
| 2008/0269685 A1 | 10/2008 | Singh et al. |
| 2009/0017210 A1 | 1/2009 | Andrianov et al. |
| 2009/0035446 A1 | 2/2009 | Kwon |
| 2009/0041810 A1 | 2/2009 | Andrianov et al. |
| 2009/0043279 A1 | 2/2009 | Kaspar et al. |
| 2009/0155330 A1 | 6/2009 | Ghartey-Tagoe et al. |
| 2009/0182306 A1 | 7/2009 | Lee et al. |
| 2009/0216215 A1 | 8/2009 | Thalmann et al. |
| 2009/0234301 A1 | 9/2009 | Tomono |
| 2010/0028390 A1 | 2/2010 | Cleary et al. |
| 2010/0200494 A1 | 8/2010 | Storer |
| 2010/0228203 A1 | 9/2010 | Quan et al. |
| 2010/0247698 A1 | 9/2010 | Zhang et al. |
| 2011/0006458 A1 | 1/2011 | Sagi et al. |
| 2011/0028905 A1 | 2/2011 | Takada |
| 2011/0046638 A1 | 2/2011 | Gartstein et al. |
| 2011/0059150 A1 | 3/2011 | Kendall et al. |
| 2011/0098651 A1 | 4/2011 | Falo et al. |
| 2011/0121486 A1 | 5/2011 | Oh et al. |
| 2011/0160069 A1 | 6/2011 | Corrie et al. |
| 2011/0165236 A1* | 7/2011 | Chow ............... A61K 9/2013 424/465 |
| 2011/0177139 A1 | 7/2011 | Hyungil et al. |
| 2011/0276027 A1 | 11/2011 | Trautman et al. |
| 2011/0276028 A1 | 11/2011 | Singh et al. |
| 2011/0280800 A1 | 11/2011 | Wu et al. |
| 2011/0288484 A1 | 11/2011 | Kendall et al. |
| 2011/0288485 A1 | 11/2011 | Tokumoto et al. |
| 2011/0295205 A1 | 12/2011 | Kaufmann et al. |
| 2011/0306853 A1 | 12/2011 | Black et al. |
| 2012/0052120 A1 | 3/2012 | Castor |
| 2012/0123297 A1 | 5/2012 | Brancazio |
| 2012/0123387 A1 | 5/2012 | Gonzalez et al. |
| 2012/0126297 A1 | 5/2012 | Brancazio |
| 2012/0130306 A1 | 5/2012 | Terahara et al. |
| 2012/0150023 A1 | 6/2012 | Kaspar et al. |
| 2012/0184906 A1 | 7/2012 | McAllister |
| 2012/0330250 A1 | 12/2012 | Kuwahara et al. |
| 2013/0131598 A1 | 5/2013 | Trautman et al. |
| 2013/0150822 A1* | 6/2013 | Ross ............... A61M 37/0015 604/501 |
| 2013/0287832 A1 | 10/2013 | O'Hagan et al. |
| 2013/0292868 A1 | 11/2013 | Singh et al. |
| 2013/0292886 A1 | 11/2013 | Sagi et al. |
| 2013/0303502 A1* | 11/2013 | Cavanagh ............... C07J 3/005 514/180 |
| 2014/0148846 A1 | 5/2014 | Pereira et al. |
| 2014/0180201 A1* | 6/2014 | Ding ............... B29C 43/021 604/46 |
| 2014/0248312 A1 | 9/2014 | Rappuoli et al. |
| 2014/0257188 A1 | 9/2014 | Kendall et al. |
| 2014/0272101 A1 | 9/2014 | Chen et al. |
| 2014/0276366 A1 | 9/2014 | Bourne et al. |
| 2014/0276378 A1 | 9/2014 | Chen et al. |
| 2014/0276474 A1 | 9/2014 | Ding et al. |
| 2014/0276580 A1 | 9/2014 | Le et al. |
| 2014/0276589 A1 | 9/2014 | Bayramov et al. |
| 2014/0330198 A1* | 11/2014 | Zhang ............... A61K 38/29 604/46 |
| 2015/0079133 A1 | 3/2015 | Ghartey-Tagoe et al. |
| 2015/0238413 A1 | 8/2015 | Mochizuki et al. |
| 2015/0297878 A1 | 10/2015 | Singh et al. |
| 2016/0058992 A1 | 3/2016 | Chen et al. |
| 2016/0067176 A1 | 3/2016 | Ding et al. |
| 2016/0135895 A1 | 5/2016 | Faasse et al. |
| 2016/0175572 A1* | 6/2016 | Crowley ............... A61K 9/0024 604/500 |
| 2016/0374939 A1 | 12/2016 | Shastry et al. |
| 2017/0050010 A1 | 2/2017 | Mcallister et al. |
| 2017/0217656 A1 | 8/2017 | Yamada |
| 2017/0281535 A1 | 10/2017 | Singh et al. |
| 2017/0361079 A1 | 12/2017 | Trautman et al. |

FOREIGN PATENT DOCUMENTS

| | | | |
|---|---|---|---|
| CA | 2316534 | 3/2001 | |
| CA | 2422907 | 4/2002 | |
| CA | 2889500 A1 * | 5/2014 | ........ A61K 31/203 |
| CA | 2889500 A1 * | 5/2014 | ........ A61K 2300/00 |
| CN | 102000020 A | 6/2011 | |
| CN | 102580232 A | 7/2012 | |
| DE | 02319591 | 11/1974 | |
| DE | 19518974 | 11/1995 | |
| DE | 19624578 | 1/1998 | |
| EP | 0156471 | 10/1985 | |
| EP | 0240593 | 10/1987 | |
| EP | 0301599 | 2/1989 | |
| EP | 0305123 A1 | 3/1989 | |
| EP | 0312662 | 4/1989 | |
| EP | 0400249 | 12/1990 | |
| EP | 0407063 | 1/1991 | |
| EP | 0796128 | 9/1997 | |
| EP | 1086718 A1 | 3/2001 | |
| EP | 1086719 A1 | 3/2001 | |
| EP | 1174078 | 1/2002 | |
| EP | 2283809 A1 | 2/2011 | |
| EP | 2399624 A1 | 12/2011 | |
| FR | 2535602 | 5/1984 | |
| GB | 0783479 | 9/1957 | |
| GB | 2221394 | 2/1990 | |
| GB | 2277202 | 10/1994 | |
| JP | 46-037758 | 12/1971 | |
| JP | 60-242042 | 12/1985 | |
| JP | 62-213763 | 9/1987 | |
| JP | 01-264839 | 10/1989 | |
| JP | 02-009755 | 3/1990 | |

(56) References Cited

FOREIGN PATENT DOCUMENTS

| | | |
|---|---|---|
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-000728 A | 1/2002 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2003-534881 A | 11/2003 |
| JP | 2004-065775 A | 3/2004 |
| JP | 2006-271781 A | 10/2006 |
| JP | 2006-341089 A | 12/2006 |
| JP | 2007-130030 A | 5/2007 |
| JP | 2007-190112 A | 8/2007 |
| JP | 2007-536988 A | 12/2007 |
| JP | 2008-006178 A | 1/2008 |
| JP | 2008-074763 A | 4/2008 |
| JP | 2008-194288 A | 8/2008 |
| JP | 2009-082206 A | 4/2009 |
| JP | 2009-082207 A | 4/2009 |
| JP | 2009-201956 A | 9/2009 |
| JP | 2010-233673 A | 10/2010 |
| JP | 2010-233674 A | 10/2010 |
| KR | 20100064669 A | 6/2010 |
| RU | 2414255 C1 | 3/2011 |
| SU | 1641346 | 4/1991 |
| SU | 1667864 | 8/1991 |
| WO | WO 1993/015701 | 8/1993 |
| WO | WO 1993/017754 | 9/1993 |
| WO | WO 1994/023777 | 10/1994 |
| WO | WO 1995/022612 | 8/1995 |
| WO | WO 1995/033612 | 12/1995 |
| WO | WO 1996/000109 | 1/1996 |
| WO | WO 1996/017648 | 6/1996 |
| WO | WO 1996/037155 | 11/1996 |
| WO | WO 1996/037256 | 11/1996 |
| WO | WO 1996/038174 A1 | 12/1996 |
| WO | WO 1997/003629 | 2/1997 |
| WO | WO 1997/003718 | 2/1997 |
| WO | WO 1997/013544 | 4/1997 |
| WO | WO 1997/048440 | 12/1997 |
| WO | WO 1997/048441 | 12/1997 |
| WO | WO 1997/048442 | 12/1997 |
| WO | WO 1998/000193 | 1/1998 |
| WO | WO 1998/028307 | 7/1998 |
| WO | WO 1999/000155 | 1/1999 |
| WO | WO 1999/029298 | 6/1999 |
| WO | WO 1999/029364 | 6/1999 |
| WO | WO 1999/029365 | 6/1999 |
| WO | WO 1999/049874 A1 | 10/1999 |
| WO | WO 1999/061888 | 12/1999 |
| WO | WO 1999/064580 | 12/1999 |
| WO | WO 2000/005166 | 2/2000 |
| WO | WO 2003/026733 A2 | 4/2000 |
| WO | WO 2000/035530 | 6/2000 |
| WO | WO 2000/070406 | 11/2000 |
| WO | WO 2000/074763 A2 | 12/2000 |
| WO | WO 2000/074764 | 12/2000 |
| WO | WO 2000/074765 | 12/2000 |
| WO | WO 2000/074766 | 12/2000 |
| WO | WO 2000/077571 | 12/2000 |
| WO | WO 2001/008242 | 2/2001 |
| WO | WO 2001/036037 | 5/2001 |
| WO | WO 2001/036321 | 5/2001 |
| WO | WO 2001/049362 | 7/2001 |
| WO | WO 2002/002180 | 1/2002 |
| WO | WO 2002/007543 | 1/2002 |
| WO | WO 2002/007813 | 1/2002 |
| WO | WO 2002/017985 | 3/2002 |
| WO | WO 2002/030281 A1 | 4/2002 |
| WO | WO 2002/030301 A1 | 4/2002 |
| WO | WO 2002/032331 | 4/2002 |
| WO | WO 2002/032480 | 4/2002 |
| WO | WO 2005/046769 A2 | 5/2002 |
| WO | WO 2002/064193 A2 | 6/2002 |
| WO | WO 2002/062202 | 8/2002 |
| WO | WO 2002/072189 | 9/2002 |
| WO | WO 2002/085446 A2 | 10/2002 |
| WO | WO 2002/091922 | 11/2002 |
| WO | WO 2002/100474 | 12/2002 |
| WO | WO 2003/024290 | 3/2003 |
| WO | WO 2003/024518 | 3/2003 |
| WO | WO 2004/000389 A2 | 12/2003 |
| WO | WO 2004/009172 A1 | 1/2004 |
| WO | WO 2004/020034 A2 | 3/2004 |
| WO | WO 2004/024224 A1 | 3/2004 |
| WO | WO 2004/030649 A2 | 4/2004 |
| WO | WO 2004/076339 | 9/2004 |
| WO | WO 2004/105729 A2 | 12/2004 |
| WO | WO 2004/110717 | 12/2004 |
| WO | WO 2005/002453 A1 | 1/2005 |
| WO | WO 2005/044333 A2 | 5/2005 |
| WO | WO 2005/065765 A1 | 7/2005 |
| WO | WO 2005/067889 A1 | 7/2005 |
| WO | WO 2005/082596 A1 | 9/2005 |
| WO | WO 2005/089857 A1 | 9/2005 |
| WO | WO 2005/094526 | 10/2005 |
| WO | WO 2005/099751 A2 | 10/2005 |
| WO | WO 2005/112984 A2 | 12/2005 |
| WO | WO 2006/020842 | 2/2006 |
| WO | WO 2006/055795 | 5/2006 |
| WO | WO 2006/062848 A1 | 6/2006 |
| WO | WO 2006/086742 A2 | 8/2006 |
| WO | WO 2006/101459 A1 | 9/2006 |
| WO | WO 2007/002521 A2 | 1/2007 |
| WO | WO 2007/002522 A1 | 1/2007 |
| WO | WO 2007/002523 | 1/2007 |
| WO | WO 2007/012114 A1 | 2/2007 |
| WO | WO 2007/030477 A2 | 3/2007 |
| WO | WO 2007/061964 A1 | 5/2007 |
| WO | WO 2007/061972 A2 | 5/2007 |
| WO | WO 2007/075806 A2 | 7/2007 |
| WO | WO 2007/081430 A2 | 7/2007 |
| WO | WO 2007/124411 | 11/2007 |
| WO | WO 2008/011625 | 1/2008 |
| WO | WO 2008/015236 A1 | 2/2008 |
| WO | WO 2008/024141 A2 | 2/2008 |
| WO | WO 2008/091602 | 7/2008 |
| WO | WO 2008/130587 | 10/2008 |
| WO | WO 2008/139648 A1 | 11/2008 |
| WO | WO 2009/039013 A1 | 3/2009 |
| WO | WO 2009/048607 A1 | 4/2009 |
| WO | WO 2009/054988 A1 | 4/2009 |
| WO | WO 2009/142741 A1 | 11/2009 |
| WO | WO 2010/040271 A1 | 4/2010 |
| WO | WO 2010/124255 A2 | 10/2010 |
| WO | WO 2011/121023 A1 | 10/2011 |
| WO | WO 2011/140240 | 10/2011 |
| WO | WO 2011/140274 | 10/2011 |

(56) References Cited

FOREIGN PATENT DOCUMENTS

| WO | WO 2012/054582 A2 | 4/2012 |
|---|---|---|
| WO | WO 2012/101639 A2 | 8/2012 |
| WO | WO 2012/122163 A1 | 9/2012 |
| WO | WO 2012/127249 A1 | 9/2012 |
| WO | WO 2012/153266 A2 | 11/2012 |
| WO | WO 2013/172999 A1 | 11/2013 |
| WO | WO 2014/004301 A1 | 1/2014 |
| WO | WO 2014/077244 A1 | 5/2014 |
| WO | WO 2014/100750 A1 | 6/2014 |
| WO | WO 2014/144973 A1 | 9/2014 |
| WO | WO 2014/150069 A1 | 9/2014 |
| WO | WO 2014/150285 A2 | 9/2014 |
| WO | WO 2014/151654 A1 | 9/2014 |
| WO | WO 2014/164314 A1 | 10/2014 |
| WO | WO 2016/033540 A1 | 3/2016 |
| WO | WO 2016/036866 A1 | 3/2016 |
| WO | WO 2016/073908 A1 | 5/2016 |
| WO | WO 2017/004067 A1 | 1/2017 |

OTHER PUBLICATIONS

Corbett et al., "Skin vaccination against cervical cancer associated human papillpmavirus with a novel micro-projection array in a mouse model", PLOS one, vol. 5, No. 10, pp. 1-9 (2010).
Database WPI / Thomson, Accession No. 2014-V89218, Gao et al., "Soluble microneedle patch useful for transdermal administration of vaccine, comprises water-soluble polymer material as matrix material and soluble microneedle main portion", Application No. CN104027324A, Tech Inst Phys. & Chem. Chinese Acad., 3 pages (2014).
Ghosh et al., "Influence of critical parameters of nanosuspension formulation on permeability of a poorly soluble drug through the skin-A Case study", vol. 14, No. 3, pp. 1108-1117 (2013).
Guo et al., "Enhanced transcutaneous immunization via dissolving microneedle array loaded with liposome encapsulated antigen and adjuvant", Int. J. Pharm., vol. 447, No. 1-2, pp. 22-30 (2013).
Gupta, "Aluminum compounds as vaccine adjuvants", Adv. Drug Deilv. Rev., vol. 32, No. 3, pp. 155-172 (1998) Abstract Only.
Gupta and Rost, "Aluminum compounds as vaccine adjuvants", Vaccine adjuvants: Preparation Methods and Research Protocols, O'Hagan, ed., Humana Press, Inc., Totowa, New Jersey, Meth. Mol. Med., vol. 42, No. 4, No. 4, pp. 65-89 (2000).
International Search Report from International Patent Application No. PCT/US2015/047563 dated Nov. 20, 2015.
International Search Report from International Patent Application No. PCT/US2015/048161 dated Nov. 26, 2015.
Kuroda et al., "Particulate adjuvant and innate immunity: past achievements, present findings, and future prospects", Int. Rev. Immunol., vol. 32, No. 2, pp. 209-220 (2013).
Munks et al., "Aluminum adjuvants elicit fibrin-dependent extracellular traps in vivo", Blood, vol. 116, No. 24, pp. 5191-5199 (2010).
Petrovsky and Aguilar, "Vaccine adjuvants: current state and future trends", Immunol. Cell Biol., vol. 82, No. 5, pp. 488-496 (2004).
Pittman, "Aluminum-containing vaccine associated adverse events: role of route of administration and gender", Vaccine, vol. 20, pp. s48-s50 (2002).
Prausnitz, "Microneedle-based vaccines", Curr. Top. Microbiol. Immunol., vol. 333, pp. 369-393 (2009).
Sayers et al., "Vaxjo: A Web-Based Vaccine Adjuvant Database and Its Application for Analysis of Vaccine Adjuvants and Their Uses in Vaccine Development", J. Biomed. Biotechnol., vol. 2012, Article ID: 831486, 13 pages, doi:10.1155/2012/831486 (2011).
White et al., "Studies on antibody production. III, The alum granuloma", J. Exp. Med., vol. 102, No. 1, pp. 73-82 (1955).
International Search Report from International Patent Application No. PCT/US2011/035221 dated Jan. 10, 2012, application now published as International Publication No. WO2011/140240 on Nov. 10, 2011.
International Search Report from International Patent Application No. PCT/US2015/059559 dated Jan. 21, 2016.
International Search Report from International Patent Application No. PCT/US2016/039864 dated Sep. 23, 2016.
Keitel et al., "A randomized clinical trail of acellular pertussis vaccines in healthy adults: Dose-response comparisons of 5 vaccines and implications for booster immunization", J. Infect. Dis., vol. 180, pp. 397-403 (1999).
Lutrol F 68 NF, BASF Pharma Ingredients, accessed from the internet on Sep. 5, 2016 from http://www2.basf.us/Pharma/pdf/Lutrol_F_68.pdf.
Makaida et al., "Poly lactic-co-glycolic acid (PLGA) as biodegradable controlled drug delivery carrier", Polymers (Basel), vol. 3, No. 3, pp. 1377-1397 (2011).
Vitiello et al., "Development of a lipopeptide-based therapeutic vaccine to treat chronic HBV infection", J. Clin. Invest., vol. 95, pp. 341-349 (1995).
Chun, et al., "An array of hollow microcapillaries for the controlled injection of genetic materials into animal/plant cells," IEEE Workshop on Micro Electro Mechanical Systems, pp. 406-411, (1999).
"Eudragit EPO Readymix—Tates masking and moisture protection have never been easier" Evonik Industries, Evonik Industries AG, Pharma Polymers & Services, Nov. 2014.
"Extended", Merriam-Webster Online Dictionary, 6 pages, Downloaded on Sep. 7, 2010 from <http://www.merriam-webster.com/dictionary/extend>.
"Extend", Macmillian Online Dictionary, 5 pages, Downloaded on Sep. 7, 2010 from <http://www.macmillandictionary.com/dictionary/american/extend>.
Henry, et al., "Micromachined microneedles for transdermal delivery of drugs", IEEE Workshop on Micro Electro Mechanical Systems, New York, NY. pp. 494-498, (1998).
Henry, et al., "Microfabricated microneedles: A novel apporach to transdermal drug delivert", J. Pharmaceutical Science, vol. 87, No. 8, pp. 922-925, (1998).
"Heparin Pregnancy and Breast Feeding Warning", Drugs.com, Accessed Oct. 8, 2009, <http://www.drugs.com/pregnancy/heparin.html>.
International Search Report from International Patent Application No. PCT/US2000/015612 dated Sep. 7, 2000.
International Search Report from International Patent Application No. PCT/US2000/015613 dated Sep. 6, 2000.
International Search Report from International Patent Application No. PCT/US2000/015614 dated Sep. 6, 2000.
International Search Report from International Patent Application No. PCT/US2001/031977 dated Apr. 29, 2002.
International Search Report from International Patent Application No. PCT/US2001/031978 dated Apr. 29, 2002.
International Search Report from International Patent Application No. PCT/US2002/014624 dated Sep. 3, 2002.
International Search Report from International Patent Application No. PCT/US2002/029228 dated Apr. 23, 2003.
International Search Report from International Patent Application No. PCT/US2002/029245 dated Dec. 27, 2002.
International Search Report from International Patent Application No. PCT/US2004/005382 dated Nov. 25, 2004.
International Search Report from International Patent Application No. PCT/US2004/017255 dated May 24, 2005.
International Search Report from International Patent Application No. PCT/US2005/009854 dated Jul. 3, 2008.
International Search Report from International Patent Application No. PCT/US2008/000824 dated Jul. 18, 2008.
International Search Report from International Patent Application No. PCT/US2008/004943 dated Jun. 9, 2009, application now published as International Publication No. WO2008/130587 Oct. 30, 2008.
International Search Report from International Patent Application No. PCT/US2008/011635 dated Dec. 19, 2008, application now published as International Publication No. WO2009/048607 on Apr. 16, 2009.
International Search Report from International Patent Application No. PCT/US2010/032299 dated Dec. 10, 2010, application now published as International Publication No. WO2010/124255 on Oct. 28, 2010.

(56) References Cited

OTHER PUBLICATIONS

International Search Report from International Patent Application No. PCT/US2013/077281 dated Mar. 4, 2013.
International Search Report from International Patent Application No. PCT/US2014/021841 dated Aug. 11, 2014.
International Search Report from International Patent Application No. PCT/US2014/022087 dated May 23, 2014.
International Search Report from International Patent Application No. PCT/US2014/022836 dated May 9, 2015.
International Search Report from International Patent Application No. PCT/US2014/022859 dated May 26, 2014.
International Search Report from International Patent Application No. PCT/US2014/026179 dated Jul. 18, 2014.
International Search Report from International Patent Application No. PCT/US2014/029601 dated Jul. 1, 2014.
Matriano, et al., "Macroflux(R) microprojection array patch technology: A new and efficient approach for intracutaneous immunication", Pharm. Res., vol. 19, No. 1, pp. 63-70 (2002).
McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.
Mikszta, et al., "Improved genetic immunization via micromechanical disruption of skin-barrier function and targeted epidermal delivery", Nat. Med., vol. 8, No. 4, pp. 415-419, (2002).
Mikszta, et al., "Protective immunization against inhalation anthrax: A comparison of minimally invasive delivery platforms", J. Inf. Dis., vol. 191, No. 2, pp. 278-288, (2005).
Papautsky, et al., "Micromachined Pipette Arrays," MPA, Proceedings—19th international Conference—IEEE/EMBS, Chicago IL, USA, pp. 2281-2284 (1997).
Park et al., "Biodegradable polymer microneedles: Fabrication, mechanics, and transdermal drug delivery", J. Contr. Rel., vol. 104, pp. 51-66 (2005).

Park, et al., "Polymer Microneedles for Controlled-Release Drug Delivery," Pharmaceutical Research, Kluwe Academic Publishers-Plenurn Publishers, NE, vol. 23, No. 5, pp. 1008-1019 (2006).
Prausnitz, et al., "Transdermal transport efficiency during skin electroporation and iontophoresis", J. Contr. Release, vol. 38, pp. 205-217, (1996).
Prausnitz, "Transdermal delivery of macromolecules: Recent advances by modification of skin's barrier properties", ACS Symposium Serier No. 675, *Therapeutics Protein and Peptide Formulation and Delivery*, American Chemical Society, Washington DC, Chpater 8, pp. 124-153, (1997).
Rydberg, et al., "Low-molecular-weight heparin preventing and treating DVT", Am. Fam. Physician, vol. 59, No. 6, pp. 1607-1612, (1999).
Sivamani, et al., "Microneedles and transdermal applications", Exp. Opin. Drug Del., vol. 4, No. 1, pp. 19-25, (2007).
Wouters et al., "Microelectrochemical systems for drug delivery", Electrochimica Acta., vol. 42, pp. 3385-3390, (1997).
Xia, et al., "Soft Lithography", Angew. Chem. Int. Ed., vol. 37, pp. 551-575, (1998).
Xia, et al., "Soft Lithography", Annu. Rev. Mater. Sci., vol. 28, pp. 153-184 (1998).
Julinova et al., "Initiating biodegradation of polyvinylpyrrolidone in aqueous aerobic environment", Proceedings of ECOpole, vol. 6, No. 1, pp. 121-127 (2012).
Kunduru et al., "Biodegradable polymers: Medical Applications", Encyclopedia of Polymer Science and Technology, pp. 1-22 (2016) DOI: 10.1002/0471440264.pst027.pub2.
Polysorbate 80, Material Safety Data Sheet, CAS#: 9005-65-6, Science Lab.com, Inc., 14025 Smith Rd., Houston, Texas 77396, 5 pages, Last updated May 21, 2013.

\* cited by examiner

MICROSTRUCTURE ARRAY, METHODS OF MAKING, AND METHODS OF USE

CROSS-REFERENCE TO RELATED APPLICATIONS

This application claims the benefit of U.S. Provisional Application No. 62/046,098, filed Sep. 4, 2014, which is incorporated herein by reference in its entirety.

TECHNICAL FIELD

The disclosure relates generally to a method and delivery system for transdermally administering a therapeutic agent using an array of microstructures, and related features thereof.

BACKGROUND

Arrays of microneedles were proposed as a way of administering drugs through the skin in the 1970s, for example in expired U.S. Pat. No. 3,964,482. Microneedle or microstructure arrays can facilitate the passage of drugs through or into human skin and other biological membranes in circumstances where ordinary transdermal administration is inadequate. Microstructure arrays can also be used to sample fluids found in the vicinity of a biological membrane such as interstitial fluid, which is then tested for the presence of biomarkers.

Despite much initial work on fabricating microneedle arrays in silicon or metals, there are significant advantages to polymeric arrays. U.S. Pat. No. 6,451,240 discloses some methods of manufacturing polymeric microneedle arrays. Arrays made primarily of biodegradable polymers also have some advantages. U.S. Pat. No. 6,945,952 and U.S. Published Patent Applications Nos. 2002/0082543 and 2005/0197308 have some discussion of microneedle arrays made of biodegradable polymers. A detailed description of the fabrication of a microneedle array made of polyglycolic acid is found in Jung-Hwan Park et al., "Biodegradable polymer microneedles: Fabrication, mechanics, and transdermal drug delivery," J. of Controlled Release, 104:51-66 (2005).

Biodegradable polymer arrays have typically been used with water soluble drugs. The arrays are made using water soluble polymers that dissolve easily when inserted into the subject's skin. The use of water soluble polymers works well with water soluble drugs as a single phased liquid formulation can be formed.

With the advent of combinatorial chemistry and high throughput screening, the number of poorly water soluble drug candidates has dramatically increased. Poor solubility of the therapeutic agent is one of the most frequently encountered difficulties in the field of pharmaceutics.

Accordingly, it would be of benefit to develop an effective means of delivering therapeutic agents that are poorly soluble, have very low solubility in an aqueous medium, or are substantially water-insoluble via microstructures and of making use of the advantages of microstructure array delivery.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In a first aspect, an array of microstructures is provided comprising an approximately planar base and a plurality of microstructures comprising a drug, wherein each of the plurality of microstructures has mechanical strength sufficient to provide transdermal administration to a subject. The microstructure comprises a backing having a first surface and a second surface opposed thereto, and a microstructure array comprising the plurality of microstructures, wherein the plurality of microstructures extend outwardly from the first surface of the backing. Each of the plurality of microstructures comprises a biodegradable, water soluble distal layer and at least one proximal layer positioned between the distal layer and the first surface of the backing. The distal layer comprises at least one drug and a stabilizing excipient.

In one aspect, a microstructure apparatus comprising a backing having a first surface and a second surface opposed thereto and a microstructure array comprising a plurality of microstructures extending outwardly from the first surface of the backing is described. Each of the plurality of microstructures comprises a biodegradable distal layer. Further, the distal layer comprises (i) at least one therapeutic agent that is poorly soluble in water or an aqueous solvent, and (ii) one or more polymers, the polymers being selected from polymers that (a) are soluble in an aqueous solvent and are soluble in an organic solvent, or (b) are soluble in an organic solvent/aqueous solvent mixture. In embodiments, the backing is a UV-curable adhesive. In an embodiment, the distal layer of the apparatus further comprises at least one solubility enhancer. In embodiments, the at least one solubility enhancer is selected from an emulsifier and a solubilizer. In specific embodiments, the at least one solubility enhancer is selected from D-α tocopheryl polyethylene glycol 1000 succinate and Kolliphor.

In an embodiment, the at least one polymer is soluble in water or an aqueous solvent and the at least one polymer further includes hydrophilic properties. In embodiments, the at least one polymer is selected from a starch derivative, polysaccharide, polyvinyl alcohol (PVA), and polyvinyl pyrrolidone (PVP). In further embodiments, the starch derivative is hetastarch. In yet another embodiment, the polysaccharide is dextran.

In embodiments, the therapeutic agent has a solubility in water or an aqueous solvent of less than about 10 mg/mL to about 1 mg/mL. In further embodiments, the therapeutic agent has a solubility in water or an aqueous solvent of less than about 1 mg/mL to about 100 µg/mL. In yet other embodiments, the therapeutic agent has a solubility in water or an aqueous solvent of less than about 100 µg/mL. In other embodiments, the therapeutic agent has a solubility in water or an aqueous solvent of less than about 50 µg/mL. In additional embodiments, the therapeutic agent has a solubility in water or an aqueous solvent of less than about 30 µg/mL. In further embodiments, the therapeutic agent has a solubility in water or an aqueous solvent of less than about 1 µg/mL.

In a further embodiment, the apparatus further includes a substrate having a first surface and a second surface opposed thereto. The second surface of the backing is affixed to the first surface of the substrate.

In a further aspect, a method for making a microstructure array comprises the steps of (a) mixing (i) a therapeutic agent that is poorly soluble in an aqueous solvent, and (ii) one or more polymers in (iii) a solvent selected from an organic solvent and an organic solvent/aqueous solution mixture to form a polymer solution or suspension; (b) dispensing the polymer solution or suspension on a mold having an array of microstructure cavities; (c) filling the microstructure cavities in the mold; (d) removing excess solution or suspension on the mold surface; and (e) drying the solution or suspension at about 5° C. to 50° C. to form an array of microstructures. In an embodiment, the step of drying the solution comprises drying the solution or suspension in a chamber having at least one of (i) a partial pressure of about 30 psi to 60 psi at a temperature of about 5° C. to 50° C.; or (ii) an atmosphere filled with solvent of the liquid casting formulation at a temperature of about 5° C. to 50° C. In a further embodiment, the method comprises (f) drying the microstructure under vacuum at about 5° C. to 50° C. In another embodiment the chamber uses convection, conduction or radiation for drying. In another embodiment, the method further includes a solubility enhancer in step (a).

In another embodiment, the method further comprises (g) dissolving a polymer in a second organic solvent to form a backing polymer solution or suspension. Neither of the therapeutic agent nor the one or more polymers of step (a) are appreciably soluble in the second organic solvent and the method further includes (h) dispensing a basement or backing layer on the mold surface; and (i) drying the basement or backing layer. In a further embodiment, the method further comprises (g) dissolving a polymer in a second organic solvent to form a backing polymer solution or suspension, (h) dispensing a basement or backing layer on the mold surface; and (i) drying the basement or backing layer. The polymer solution or suspension and the backing polymer solution or suspension do not appreciably mix.

In further embodiments, less than about 50% of the active agent is present in the backing polymer solution or suspension. In another embodiment, less than about 40% of the active agent is present in the backing polymer solution or suspension. In an additional embodiment, less than about 30% of the active agent is present in the backing polymer solution or suspension. In an embodiment, less than about 20% of the active agent is present in the backing polymer solution or suspension. In other embodiments, less than about 10% of the active agent is present in the backing polymer solution or suspension. In a further embodiment, less than about 5% of the active agent is present in the backing polymer solution or suspension.

In embodiments, drying the basement or backing layer comprises drying in an oven at about 5° C. to 50° C. In a further embodiment, the method further comprises affixing the basement or backing layer to a substrate. In yet another embodiment, the method further comprises attaching a UV curable adhesive backing layer to the microstructure array.

In other embodiments, the solvent is selected from ethanol, isopropyl alcohol, acetonitrile, DMSO, and NMP. In another embodiment, the organic solvent/aqueous solution mixture is selected from ethanol:$H_2O$, and isopropyl alcohol:$H_2O$. In a further embodiment, the mixture comprises the organic solvent and $H_2O$ in a ratio of about 10:90 to about 90:10. In embodiments, the organic solvent/aqueous solution mixture is selected from DMSO:$H_2O$, and NMP:$H_2O$. In additional embodiments, the mixture comprises the DMSO and $H_2O$ in a ratio of about 10:90 to about 90:10. In yet further embodiments, the mixture comprises the NMP and $H_2O$ in a ratio of about 10:90 to about 90:10.

BRIEF DESCRIPTION OF DRAWINGS

FIG. 3 is a plot of drug purity and stability (%) over 1 or 2 weeks after storage at 4° C. or 25° C.

FIG. 6A depicts a microstructure having a pyramidal tip with a funnel shaped distal portion. FIG. 6B depicts a microstructure having a conical tip, a cylindrical shank and a conical funnel distal portion.

Figure 1A:
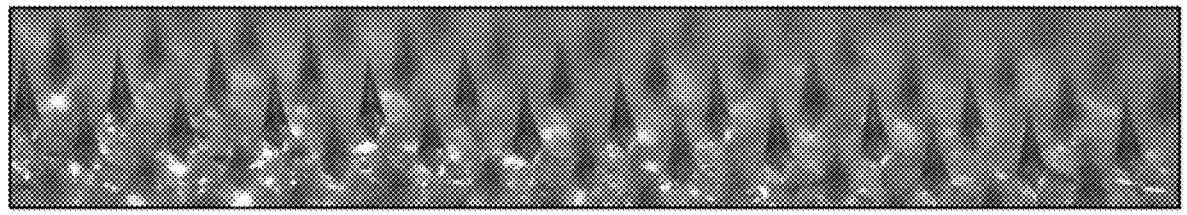
FIGS. 1A-1B are images of microprojection arrays showing intact arrays (FIG. 1A) and arrays after exposure to rat serum (FIG. 1B).

It will be appreciated that the thicknesses and shapes for the various microstructures have been exaggerated in the drawings to facilitate understanding of the device. The drawings are not necessarily "to scale".

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g. A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

I. DEFINITIONS

As used in this specification, the singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

In describing and claiming the present invention, the following terminology will be used in accordance with the definitions described below.

"Optional" or "optionally" means that the subsequently described circumstance may or may not occur, so that the description includes instances where the circumstance occurs and instances where it does not.

"Substantially" or "essentially" means nearly totally or completely, for instance, 90-95% or greater of some given quantity.

"Biodegradable" refers to natural or synthetic materials that degrade enzymatically, non-enzymatically or both to produce biocompatible and/or toxicologically safe by-products which may be eliminated by normal metabolic pathways.

"Hydrophobic polymer" as used herein refers to polymers that are insoluble or poorly soluble in aqueous solvents. "Hydrophilic polymer" as used herein refers to polymers that are soluble or substantially soluble in aqueous solvents.

The terms "microprotrusion", "microprojection", "microstructure" or "microneedle" are used interchangeably herein to refer to elements adapted to penetrate or pierce at least a portion of the stratum corneum or other biological membranes. For example, illustrative microstructures may include, in addition to those provided herein, microblades as described in U.S. Pat. No. 6,219,574, edged microneedles as described in U.S. Pat. No. 6,652,478, and microprotrusions as described in U.S. Patent Publication Nos. U.S. 2008/0269685 and U.S. 2009/0155330, each of which is incorporated herein by reference.

"Transdermal" refers to the delivery of an agent into and/or through the skin for local and/or systemic therapy. The same inventive principles apply to administration through other biological membranes such as those which line the interior of the mouth, gastro-intestinal tract, blood-brain barrier, or other body tissues or organs or biological membranes which are exposed or accessible during surgery or during procedures such as laparoscopy or endoscopy.

A material that is "water-soluble" may be defined as soluble or substantially soluble in aqueous solvents, such that the material dissolves into, within or below the skin or other membrane which is substantially aqueous in nature.

A material that is "poorly water-soluble" or has "very low water solubility" may be defined as not appreciably and/or not substantially soluble in water or an aqueous solvent. In embodiments, poorly soluble is defined in the Biopharmaceutical Classification System (BCS) as not being soluble for a dose in ≤250 mL of aqueous media over the range pH 1-pH 7.5.

A material that is "slightly soluble" may be defined as having a solubility of about 10 mg/mL to about 1 mg/mL at 25° C. or 100-1000 parts of solvent required for one part solute at 25° C. (USP). A material that is "very slightly soluble" and/or "practically insoluble" may be defined as having a solubility of about 1 mg/mL to about 100 μg/mL at 25° C. or 1000-1000 parts solvent required for one part solute (USP). A material that is "insoluble" refers to an active agent which does not appreciably dissolve in water and/or does not form a homogenous single phase with water. According to USP, an agent that is practically insoluble or insoluble requires greater than or equal to 10,000 solvent for one part solute. In embodiments, a material that is "insoluble" may be defined as having a solubility of less than about 10 mg/mL. In other embodiments, a material that is "insoluble" may be defined as having a solubility of less than about 100 μg/mL. In further embodiments, a material that is "insoluble" may have a solubility in water less than about 10 mg/ml at 25° C., less than about 5 mg/ml at 25° C., less than about 1 mg/ml at 25° C., or less than about 0.5 mg/ml at 25° C.

II. MICROSTRUCTURE ARRAYS

Provided herein are compositions and methods for transdermal administration of an active agent, drug or therapeutic agent that is poorly soluble, has low to very low solubility, or is insoluble in water and/or an aqueous solvent using an array of microprojections. Hereafter, description or features described with reference to an active agent, therapeutic agent, or drug that is poorly soluble in water or an aqueous solvent also applies to an active agent, therapeutic agent, or drug that has low to very low solubility or is insoluble in water and/or an aqueous solvent. General features of microstructure arrays suitable for use in the instant arrays and methods are described in detail in U.S. Patent Publication No. 2008/0269685, U.S. Patent Publication No. 2009/0155330, U.S. Patent Publication No. 2011/0006458, and U.S. Patent Publication No. 2011/0276028, the entire contents of which are explicitly incorporated herein by reference.

In general, the microstructure array includes a plurality of microstructures. At least a portion of the microstructures include a distal layer or end that comprises (i) at least one therapeutic agent that is poorly soluble, has low to very low solubility or is insoluble in an aqueous solvent, and (ii) one or more polymers. The one or more polymers are selected from polymers that (a) are soluble in an aqueous solvent and are soluble in an organic solvent, or (b) are soluble in an organic solvent/aqueous solvent mixture. At least a portion of the microstructures may include at least one solubility enhancer. The array may also include a backing where the microstructures extend outwardly from one surface of the backing.

Figure 4:
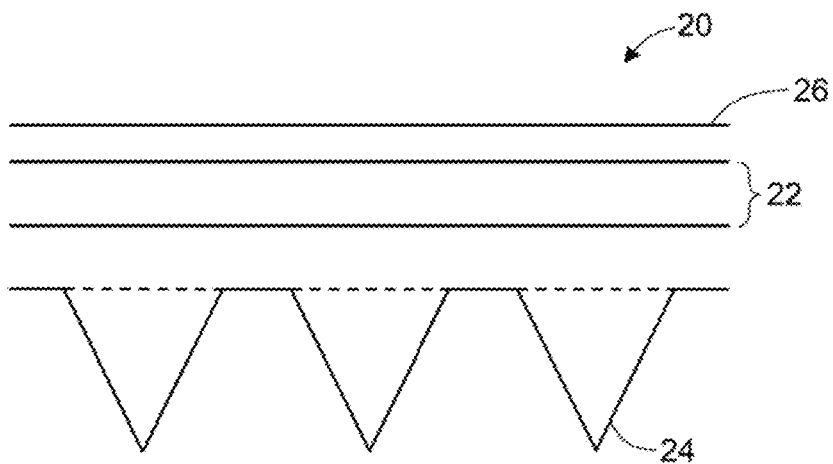
FIG. 4 is an illustration of an exemplary microstructure array.

FIG. 4 is an illustration of an exemplary microstructure array 20. The array includes a plurality of microstructures 24 adjacent a backing layer or base 22. The active agent is contained at least in the microstructures. The array may further include a substrate 26 adjacent the backing layer. The microstructures may include one or more layers with similar or different compositions. In an embodiment, each of the plurality of microstructures is at least partially formed of a biodegradable polymer matrix. Preferably, at least the distal ends of the microstructures are formed of the biodegradable, bioerodible, and/or water soluble polymer matrix. The biodegradable polymer matrix comprises at least one structure forming polymer and an active agent. Preferably, the microstructures distal ends, upon penetration of a subject's skin, undergo dissolution to thereby deliver the active agent.

In embodiments, the active agent is poorly soluble, has very low solubility, is practically insoluble, not appreciably soluble or is insoluble in water and/or an aqueous agent. In embodiments, the poorly soluble active agent is classified as Class II or Class IV according to the Biopharmaceutics Classification System (BCS). Class II agents have low solubility and high permeability. Class IV agents have low solubility and low permeability.

About 30% of drugs on the World Health Organization (WHO) list of essential drugs are poorly water soluble, based on the BCS. Further, about 40% of newly developed active substances have solubility issues. Factors that influence solubility include particle size, amorphous vs. crystalline forms, anhydrous vs. hydrous forms, and salt form vs. non-salt form. In general, agents that are at least one of larger size, crystalline forms, hydrate forms, and non-salt forms have lower aqueous or water solubility. In addition, some agents with a higher molecular weight have a lower aqueous or water solubility.

Solubility is the property of a solute (a solid, liquid, or gaseous substance) that will dissolve in a solvent to form a homogenous solution. Solubility may be stated in units of concentration, molarity, mole fraction, mole ratio, or other acceptable units. Solubility is commonly expressed as a concentration of mass of solute per mass of solvent. Solubility may be measured by at least one of kinetic solubility measurement, thermodynamic solubility, and/or may be estimated or predicted using a solubility model. Kinetic solubility may be measured by turbidity, nephelometry, or UV absorption for example. Thermodynamic solubility methods include the shake-flask method and/or a solvent evaporation method. Predictive models include, but are not limited to fragment-based models and/or models based on log P.

Suitable active agents that may be administered include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In embodiments, the active agent is a biological agent including, but not limited to, peptides, polypeptides, proteins, or nucleic acids (e.g. DNA or RNA). Many peptides and proteins are poorly soluble in water and/or an aqueous solution. The solubility of peptides and proteins is mainly determined by its polarity. Peptides and proteins containing 50% or more hydrophobic residues (F, I, L, M, V, W, Y) may be insoluble or only partially soluble in water or aqueous solutions. Peptides and proteins containing 75% or more hydrophobic residues are generally insoluble in water or aqueous solutions.

In one embodiment, the active agent is a peptide, polypeptide or protein which is insoluble or poorly soluble in an aqueous solution. Membrane proteins are often insoluble or poorly soluble in an aqueous solution. Additionally, proteins and peptides having a significant or high proportion of hydrophobic residues are often insoluble or poorly soluble in an aqueous solution. Examples of peptides and proteins which may be used with the microstructure arrays include, but are not limited to, insoluble hormones such as steroid hormones and insulin, and pharmacologically active salts thereof. Further exemplary peptides are hydrophobically modified peptides such as GLP-1 receptor agonists. One particular peptide contemplated is Liraglutide, a $C_{16}$ fatty acid modified GLP-1.

Biodegradable polymers currently used in microstructure arrays are typically water soluble. The active agent is mixed with the polymer to form a polymer matrix or suspension. However, the active agents contemplated herein are poorly soluble, have very low solubility, are practically insoluble, are not appreciably soluble or are insoluble in water and/or aqueous solvents, which are typically used with the biodegradable polymers. Therefore, a single phase aqueous formulation can't be obtained. It follows that the resulting polymer matrix will not have the active agent dispersed evenly therein resulting in uneven delivery of the agent to the skin. The present arrays and methods provide a solution for delivery of agents that are poorly soluble, have low solubility, are not appreciably soluble, or are insoluble in water or an aqueous solution.

In embodiments, the active agent has a solubility in water and/or an aqueous solvent of less than or equal to about 10 mg/mL to 1 mg/mL. In other non-limiting embodiments, the active agent has a solubility in water and/or an aqueous solvent of less than or equal to about 1 mg/mL-100 µg/mL, 1-100 µg/mL, 1-50 µg/mL, 1-25 µg/mL, 25-100 µg/mL, 30-100 µg/mL, or 50-100 µg/mL. In specific, but not limiting embodiments, the active agent has a solubility in water and/or an aqueous solvent of less than or equal to about 10 mg/mL, 1 mg/mL, 100 µg/mL, 50 µg/mL, 30 µg/mL, or 1 µg/mL.

At least a portion of the microstructures as described in the patent publications referred to above are formed of a biodegradable, bioerodible, bioabsorbable and/or biocompatible polymer matrix. The polymers for the polymer matrix should be soluble in a solvent that is compatible with the poorly soluble agent. In one embodiment, the polymer is soluble in an aqueous solvent as well as soluble in an organic solvent. In another embodiment, the polymer is soluble in an organic solvent/aqueous solvent mixture. It will be appreciated that solubility in the solvent need only be suitably soluble to dissolve the required amount of polymer in the solvent. Suitable polymers include, but are not limited to starch derivatives, polysaccharides, polyvinyl alcohol (PVA), polyacrylic acid, poly(2-hydroxyl-ethyl methacrylate), and polyvinyl pyrrolidone (PVP). In an embodiment, the starch derivative is hetastarch. In another embodiment, the polysaccharide is dextran. Further suitable polymers are polymers that are soluble in water or an aqueous solvent and further include hydrophobic properties. Polymers for use in the described microprojection array are preferably biocompatible, biodegradable, bioabsorbable and/or bioerodible. Suitable polymers typically, but not always, have polar groups such as hydroxyl, carboxyl, aminal, amide, ketone, or ether groups.

Delivery of the active agent may be facilitated or enhanced by the inclusion of one or more solubility enhancers in the microstructures. Solubility enhancers may enhance solubility of the agent and/or polymer in the solvent and/or enhance solubility of the agent upon release at the administration site. Suitable solubility enhancers include, but are not limited to, emulsifiers and solubilizers. Specific solubility enhancers include, but are not limited to D-α tocopheryl polyethylene glycol 1000 succinate (VitE TPGS) and non-ionic solubilizers and emulsifiers, such as a polyethoxylated castor oil like those sold under the tradename Kolliphor®, Polysorbate, Macrogol 15 Hydroxystearate sold under the tradename Solutol®, Amphiphlic bi-block copolymers, and tri-block copolymers, such as PEG-PPG, PEG-PPG-PEG, PEG-PLA, PLA-PEG-PLA, PLGA-PEG, PLGA-PEG-PLGA, etc.

The biodegradability or dissolvability of the microprojection arrays as described in the above-referenced patent publications may be facilitated by the inclusion of one or more sugars. Exemplary sugars include dextrose, fructose, galactose, maltose, maltulose, iso-maltulose, mannose, lactose, lactulose, sucrose, and trehalose. Sugar alcohols, for example lactitol, maltitol, sorbitol, and mannitol, may also be employed. Cyclodextrins can also be used advantageously in microneedle arrays, for example $\alpha$, $\beta$, and $\gamma$ cyclodextrins, for example hydroxypropyl-$\beta$-cyclodextrin and methyl-$\beta$-cyclodextrin. Sugars and sugar alcohols may also be helpful in stabilization of peptides and proteins and in modifying the mechanical properties of the microprojections by exhibiting a plasticizing-like effect.

The biodegradability of a microstructure array as described in the above-referenced patent publications may also be facilitated by inclusion of water-swellable polymers such as crosslinked PVP, sodium starch glycolate, crosslinked polyacrylic acid, crosscarmellose sodium, celluloses, natural and synthetic gums, polysaccharides, or alginates. In a multilayer array, the sugars and other polymers which facilitate biodegradability may be located only in a layer or layers which encompass the microprojections.

Further examples of components that may be employed in pharmaceutical formulations are presented in Remington's Pharmaceutical Sciences, 16$^{th}$ Ed. (1980) and 20$^{th}$ Ed. (2000), Mack Publishing Company, Easton, Pa.

Generally, the number of microstructures in the array is preferably at least about 50, at least about 100, at least about 500, at least about 1000, at least about 1400, at least about 1600, at least about 2000, at least about 3000, or at least about 4000. For example, the number of microstructures in the array may range from about 1000 to about 4000, or about 1000 to about 3000, or from about 2000 to about 4000, or from about 2000 to about 3500, or from about 2000 to about 3000, or from about 2200 to about 3200. The area density of microstructures, given their small size, may not be particularly high, but for example the number of microstructures per cm$^2$ may be at least about 50, at least about 250, at least about 500, at least about 750, at least about 1000, at least about 2000, or at least about 3000 microstructures per cm$^2$ or more.

While the array itself may possess any of a number of shapes, the array is generally sized to possess a diameter cross-length of from about 5 millimeters (mm) to about 25 mm, or from about 7 mm to about 20 mm, or from about 8 mm to about 16 mm. Exemplary diameters include 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, and 25 mm.

The sizes of the microneedles and other protrusions for use with the present array will be a function of the manufacturing technology and of the precise application. In general, however, microstructures and other microprotrusions used in practice may be expected to have a height of at least about 20 µm to about 1000 µm, more preferably from about 50 µm to about 750 µm and most preferably from about 100 µm to about 500 µm. In specific, but not limiting embodiments, the microstructures have a height of at least about 100 µm, at least about 150 µm, at least about 200 µm, at least about 250 µm, at least about 300 µm, at least about 350 µm, at least about 400 µm, at least about 450 µm, or at least about 500 µm. In general it is also preferred that the microprojections have a height of no more than about 1 mm, no more than about 500 µm, no more than about 300 µm, or in some cases no more than about 200 µm or 150 µm. Often it will be desired that the microprotrusions will be long enough to penetrate at least partially through the stratum corneum layer of skin at some suitable point of application on the human body, for example the thigh, hip, arm, or torso. In embodiments, the microprojections may have an aspect ratio of at least 3:1 (height to diameter at base), at least about 2:1, or at least about 1:1.

The microprojections may have any suitable shape including, but not limited to polygonal or cylindrical. Particular embodiments include pyramidal including a four-sided pyramid, a funnel shape, a cylinder, a combination of funnel and cylinder shape having a funnel tip and a cylindrical base, and a cone with a polygonal bottom, for example hexagonal or rhombus-shaped. Other possible microprojection shapes are shown, for example, in U.S. Published Patent App. 2004/0087992 and in U.S. Application No. 61/745,513 published as US 2014/0180201, each of which are incorporated herein by reference. Microprojections may in some cases have a shape which becomes thicker towards the base, for example microprojections which have roughly the appearance of a funnel, or more generally where the diameter of the microprojection grows faster than linearly with distance to the microprojection distal end. It will be appreciate that polygonal microprojections may also have a shape which becomes thicker toward the base or where a radius or diameter grows faster than linearly with distance to the microprojection distal end. Where microprojections are thicker towards the base, a portion of the microprojection adjacent to the base, which may be called the "foundation," may be designed not to penetrate the skin.

Figure 5C:
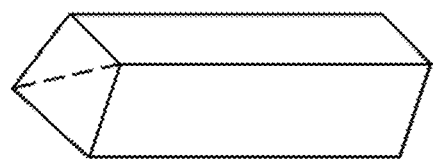
FIGS. 5A-5C are illustrations of exemplary shapes for microstructures of the arrays described herein.
Figure 5B:
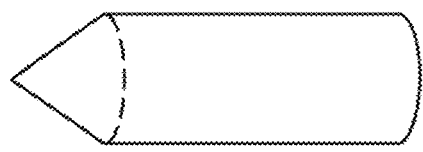
Figure 5A:
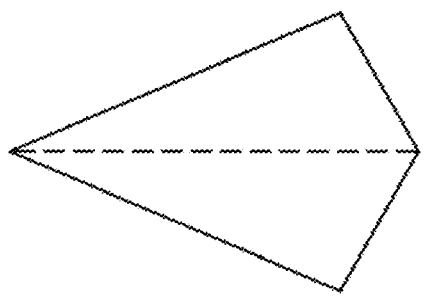

One illustrative shape for the microstructures is a cone with a polygonal bottom, for example, being hexagonal or rhombus-shaped. Additional microstructure shapes include those provided, for example, in U.S. Patent Publication No. 2004/0087992. In embodiments, at least a portion of the microstructure shape may be substantially cylindrical, cone-shaped, funnel-shaped, or pyramidal. In further embodiments, at least a portion of the microstructures has an asymmetrical cross-dimensional shape. Suitable asymmetric shapes include, but are not limited to, rectangular, square, oval, elliptical, circular, rhombus, triangular, polygonal, star-shaped, etc. In some embodiments, the distal layer has a cross-dimension in one direction that is smaller than the cross-dimension in the other direction. Exemplary cross-dimensional shapes with this configuration include, but are not limited to, rectangular, rhombus shaped, ellipse, and oval (see FIGS. 5A-5C for non-limiting examples). It will further be appreciated that different portions and/or layers of a microstructure may have different cross-dimensional shapes. At least a portion of the microstructures may include one or more blade or piercing elements along its length and/or at the distal tip. In some embodiments, at least a portion of the microstructures have a sharp, pointed, or spike-shaped distal end.

Figure 6A:
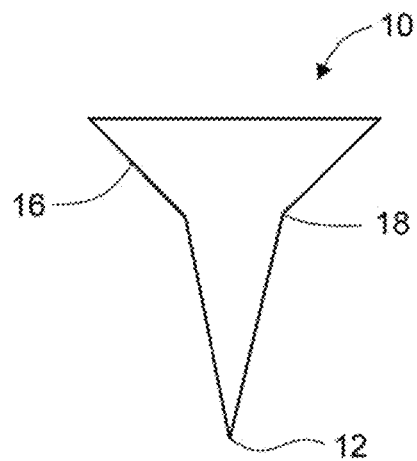
FIGS. 6A-6B are illustrations of exemplary shapes for microstructures including a funnel shape.
Figure 6B:
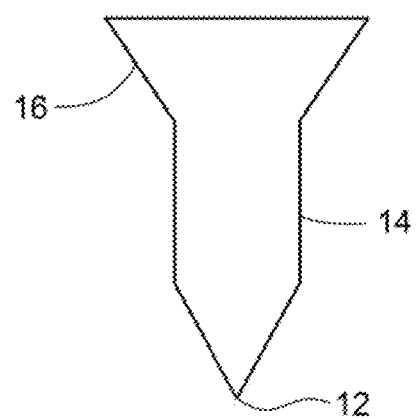

In some embodiments, microstructure shape can be understood in terms of a tip, a shank and a funnel. The angle at the tip is the apex angle—included angle by the planes or cone—and can have values from about 5 degree to about 60 degrees. The straight or substantially straight shank may or may not be present in a particular microstructure design. At the base of the shank or tip, towards the distal end, the included angle has a discontinuity or a point of inflection. The included angle jumps to take on a value greater than the apex angle for a shank-less tip and to greater than 0 degrees for microstructures with a shank. Portions of the microstructure beyond this point of inflection may be referred to as a "funnel". FIGS. 6A and 6B show examples of cross sectional elevation of the microstructures 10 delineating different regions including the tip 12, shank 14, inflection point or edge 18 and the funnel 16. In FIG. 6A, the diameter of the microstructure is growing faster than linear fashion with respect to the distance from the distal end. FIG. 1A shows a microstructure array comprising a plurality of microstructures formed in accord with Example 1. The microstructures of FIG. 1A have a sharp distal end. As in FIG. 6A, the diameter of the microstructures of FIG. 1A grow faster than linearly moving from the distal tip to the proximal end. Where microstructures are thicker towards the base, a portion of the microstructure adjacent to the base, which may be referred to herein as a "proximal portion" "backing portion", "basement", "foundation", or as an "upper portion", may be designed not to penetrate the skin.

The proximal funnel shape allows for relatively larger volumes to be dispensed in the microstructure mold for a given total length of the microstructure. The proximal funnel shape provides a larger volume (to fill) without requiring a proportional increase in microstructure height, which results in a longer drug containing portion in the microstructure. Thus, the proximal funnel shape allows for a larger solid volume for the distal portion of the microstructure with a single fill of the mold. Other shapes may require several fill and dry cycles to achieve the same amount of solid distal portion as one fill and dry cycle for the funnel shaped microstructures.

In one exemplary embodiment, at least a portion of the microstructures have a cylindrical funnel shape. Microstructures with this shape have a cylindrical shank and an optional funnel at the proximal end. In this embodiment, the distal tips of the microstructures typically, but not always, have a sharp, pointed or conical distal end to ease and/or facilitate penetration. The microstructures may further have a funnel shape at the proximal end and a cylindrical shank between the distal and proximal ends.

The funnel portion may also be used to limit the depth of penetration. Since the funnel has a several times higher volume per unit height than the tip or shank, it also requires several times higher energy to penetrate per unit depth than the tip or shank. Hence for a given energy, the microstructure may penetrate no more than the length of the tip and shank. The funnel thus can effectively act as the design element in the microstructure that limits the depth of penetration thereby ensuring tolerable sensation. It will be appreciated that other proximal end shapes may be used to limit or otherwise affect penetration of the microstructures. This is true especially where the proximal end has a larger diameter or cross-section than the shaft or middle section of the microstructures.

In embodiments, the microstructures have a sharp point or tip at a distal end or portion. A tip diameter of less than about 5 μm or 2 μm may be desirable. A tip diameter of less than about 1.5 μm is preferred, as is a tip diameter of less than about 1 μm.

The microprojections may be spaced about 0-500 μm apart. In specific, but not limiting embodiments, the microprojections are spaced about 0 μm, about 50 μm, about 100 μm, about 150 μm, about 200 μm, about 250 μm, about 300 μm, about 350 μm, about 400 μm, about 450 μm, or about 500 μm apart. The space between the microprojections may be measured from the base of the microprojections (base to base) or from the tip (tip to tip).

In further embodiments, at least a portion of the microprojections may be detachable from the microprojection array. Detachable microprojection arrays are described in U.S. Patent Publication 2009/0155330 and in U.S. Patent Application No. 2014/0180201, each of which is incorporated herein by reference. It will be appreciated that a portion of the microstructure itself may detach as opposed to detachment of a coating on the exterior of the microstructure. Detachable microprojection arrays may be accomplished by a number of approaches including, but not limited to, a layered approach in which the array is composed of multiple layers, and a layer comprising the areas where the microprojections attach to the base of the array is more readily degradable than other layers.

One potential advantage of detaching microprojections is elimination of sharp disposal requirements. Another potential advantage of detaching microprojections is elimination of needle stick injury. Another potential advantage of detaching microprojections is elimination of misuse, for example needle sharing, since the substrate without microprojections or with microprojections whose tips have been blunted due to biodegradation will not penetrate the skin. Another potential advantage of detaching microprojections is the avoidance of drug misuse because drug enriched tips are dissolved in the skin and no or minimal drug is left in the array.

Alternatively, an array made of a homogeneous material may be employed, in which the material is more readily degradable at lower pH's. Arrays made of such a material will tend to degrade more readily near the attachment points because these, being closer to the surface of the skin, are at a lower pH than the distal ends of the microprojections. (The pH of the skin's surface is generally lower than that of the skin further inwards, pH being for example approximately 4.5 on the surface and approximately 6.5 to 7.5 inward).

Materials whose solubility is dependent on pH can be, for example, insoluble in pure water but dissolve in acidic or basic pH environment. Using such materials or combination of materials, the arrays can be made to differentially biodegrade at the skin surface (PH approximately 4.5) or inside the skin. In the former, the whole array can biodegrade while in the latter, the microprojection portion of the array will biodegrade allowing the base substrate to be removed and discarded.

Materials whose degradability in an aqueous medium is dependent on pH may be made, for example, by utilizing the acrylate copolymers sold by Rohm Pharma under the brand name Eudragit, which are widely used in pharmaceutical formulation. A further example of a material with pH-dependent solubility is hydroxypropyl cellulose phthalate. Materials with pH-dependent solubility have been developed, for example, for use as enteric coatings in oral dosage forms. See, e.g., U.S. Pat. No. 5,900,252 and *Remington's Pharmaceutical Sciences* (18th ed. 1990).

It may also be desirable for the microprojection array of the invention to comprise one or more additional layers in addition to the layer which comprises the therapeutic agent. There are a number of reasons why arrays with multiple layers may be desirable. For example, it is often desirable that, compared to the whole volume of the microprojection array, the microprojections themselves have a higher concentration of active ingredient. This is so, for example, because the microprojections can be expected in many cases to dissolve more rapidly, being in a more hydrated environment than the base of the array. Furthermore, in some protocols for array application, the array may be left in for a short period of time during which essentially only the microprojections can dissolve to a substantial extent. The desirability of placing a higher concentration of active in the projections themselves is particularly acute when the active is costly. A way to achieve a higher concentration of active in the projections themselves is to have a first active-containing layer which includes the microprojections or a substantial proportion of the microprojections, and a second layer with a reduced or zero concentration of active which includes the base or a substantial proportion of the base.

The microstructure arrays should have sufficient mechanical strength to at least partially penetrate the stratum corneum or other membrane surface of a subject. It will be appreciated that different mechanical strength will be required for application at different sites. One method for assessing mechanical strength is a skin-penetration efficiency (SPE) study as described in Example 8. Preferably, the arrays have a SPE of about 50-100%. In other embodiments, the arrays have a SPE of about 50-80%, about 50-85%, about 50-90%, about 50-95%, about 60-80%, about 60-85%, about 60-90%, about 60-95%, about 60-100%, about 75-80%, about 75-85%, about 75-90%, about 75-95%, about 75-100%, about 80-85%, about 80-90%, about 80-95%, about 80-100%, about 90-95%, and about 90-100%. In specific, non-limiting, embodiments, the arrays have a SPE of about 50%, 60%, 70%, 75%, 80%, 85%, 90%, 95%, 99%, and 100%.

Preferably, at least about 50-100% of the active agent is delivered by the MSAs described herein. Delivery efficiency may be determined by preparing the MSA and applying the MSA in vivo or in vitro. An in vitro method of determining delivery efficiency includes immersing MSA in an aqueous extraction medium for a period of time, e.g. 30 minutes). The extraction medium is then analyzed for the agent. One analysis method is SEC-HPLC. The apparent delivered dose per unit and delivery efficiency are calculated with the formulas:

Apparent delivered dose=initial drug load−residual drug

% Drug delivery efficiency=100×Apparent delivered dose/initial drug load.

In embodiments, the MSA has a delivery efficiency of at least about 50-60%, about 50-70%, about 50-75%, about 50-80%, about 50-90%, about 50-95%, about 50-99%, about 60-70%, about 60-75%, about 60-80%, about 60-90%, about 60-95%, about 60-99%, about 70-75%, about 70-80%, about 70-90%, about 70-95%, about 70-99%, about 75-80%, about 75-90%, about 75-95%, about 75-99%, about 80-90%, about 80-95%, about 80-99%, about 90-95%, about 90-99%, or about 95-99%. In specific, but not limiting, embodiments the MSA has a delivery efficiency of at least about 50%, 60%, 70%, 75%, 80%, 90%, 95%, 99%, or 100%.

III. METHODS FOR MANUFACTURING MICROPROJECTION ARRAYS

Before describing the methods of manufacture in detail, it is to be understood that the methods are not limited to specific solvents, materials, or device structures, as such may vary. It is also to be understood that the terminology used herein is for the purpose of describing particular embodiments only, and is not intended to be limiting.

Microstructure arrays that are biodegradable or bioerodible typically use hydrophilic polymers that are water soluble, at least for the portion of the microstructure that is inserted into the skin. Accordingly, the solvents used in preparing the microstructures are typically water or another aqueous solvent. A problem arises when an active agent to be included in the microstructure array is poorly soluble, has very low solubility, or is insoluble in water or aqueous solvents as the poorly soluble active agent does not appreciably dissolve in the solvent.

Techniques for the fabrication of microprojection arrays are disclosed in U.S. Provisional Patent Application Nos. 60/923,861 and 60/925,462 (the priority documents for U.S. Patent Publication No. 2008/0269685, which are incorporated by reference herein). These techniques may be applied in whole or in part in the methods forming microstructure arrays including active agents that are poorly soluble, have very low solubility, or are insoluble as described below.

Examples of forming various microstructure arrays using exemplary formulations are provided in Examples 1-4. In general, an array is prepared by (a) mixing (i) a therapeutic agent that is poorly soluble, has low to very low solubility, or is insoluble in water and/or an aqueous solvent, and (ii) one or more polymers in (iii) a solvent selected from an organic solvent and an organic solvent/aqueous solution mixture to form a polymer solution or suspension; (b) casting, applying or dispensing the polymer solution or suspension on or in a mold having an array of cavities; (c) at least partially filling the microstructure cavities in the mold; and (d) drying the solution or suspension or otherwise removing the organic solvent or organic solvent/aqueous solution mixture to form the microstructure array. The method may further include removing excess solution, suspension or formulation on the mold surface. Typically, excess formulation is scraped or wiped from the mold surface. Excess formulation may be removed from the mold surface prior to drying or removing solvent. The solvent or solvent mixture may be removed by any suitable means including, but not limited to, drying the mold filled with the casting solution, formulation, suspension or solution. In an embodiment, the mold filled with the casting solution, formulation, suspension or solution is placed in a suitable oven for drying. In an embodiment, drying or removing solvent comprises placing the mold in an oven at about 5° C. to 50° C. The microprojections themselves comprise the active agent, as opposed to having the active agent present as a coating on a microprojection or microneedle made of a biocompatible material such as a metal. Where the microstructures are not integral with a substrate and/or backing layer, the microstructures are typically affixed to the substrate and/or backing layer with an adhesive prior to demolding. The following description is with reference to a "poorly soluble" therapeutic agent for convenience. However, the description is equally applicable to a therapeutic agent that has low to very low solubility, or is insoluble in water and/or an aqueous solvent.

The molds used to form the arrays in the methods herein can be made using a variety of methods and materials. Exemplary molds and methods of making molds are described, for example, in U.S. Patent Publication No. 2008/0269685, which is incorporated by reference herein. In one exemplary embodiment, the mold is a negative mold formed from a silicone such as polydimethylsilicone. A negative mold is typically formed by preparing a master microprojection array and casting a liquid mold material over the master array. The mold is allowed to dry and harden, which results in a mold comprising cavities corresponding to the microprojections of the master array. It will be appreciated that the molds suitable for use in the present methods may be prepared according to other methods.

A casting solution, formulation, or polymer solution or suspension is formed by dissolving or suspending one or more therapeutic agents, active agents, drugs, APIs, or other substances to be transdermally delivered that are poorly soluble, have low to very low solubility, or are insoluble in water and/or an aqueous solvent and one or more polymers in a solvent to form a polymer matrix solution or suspension. The terms active agent, therapeutic agent, agent, drug, API are used interchangeably herein and discussion or reference to one is intended to include and apply to each and all terms. Similarly, the terms casting solution, formulation, and polymer solution or suspension are used interchangeably herein and discussion or reference to one is intended to include and apply to each and all terms. In one embodiment, at least one of the one or more polymers is soluble in an aqueous solvent and is also soluble in an organic solvent. In another embodiment, at least one of the one or more polymers is soluble in an organic solvent/aqueous solvent mixture. Suitable polymers are described above.

Suitable aqueous solvents include, but are not limited to, water, water with alcohols (for example, $C_1$ to $C_8$ alcohols such as isopropyl alcohol, propanol and butanol), alcohol esters, water with acetonitrile (ACN), dimethyl sulfoxide (DMSO), N-methyl pyrrolidone (NMP), or mixtures of thereof. In other embodiments, the solvents are non-aqueous. Suitable non-aqueous solvents include, but are not limited to, esters, ethers, ketones, nitrites, lactones, amides, hydrocarbons and their derivatives as well as mixtures thereof. In other non-limiting embodiments, the solvent is selected from acetonitrile (ACN), dimethyl sulfoxide (DMSO), water, or ethanol. In further embodiments, the solvent is an organic solvent/aqueous solvent mixture. It will further be appreciated that the casting solvent may comprise a mixture of aqueous and non-aqueous solvents. In one embodiment, the solvent is a mixture of ethyl alcohol and water. In another embodiment, the solvent is a mixture of isopropyl alcohol and water. In another embodiment, the solvent is a mixture of DMSO and water. In yet another embodiment, the solvent is a mixture of NMP and water. Suitable mixtures comprise about 5-95% or about 10-90% of the aqueous solvent and about 5-95% or about 10-90% of the non-aqueous solvent. In specific, but non-limiting embodiments, the solvent mixture comprises about 5-80%, 5-75%, 5-60%, 5-50%, 5-40%, 5-35%, 5-30%, 5-25%, 5-20%, 5-15%, 5-10%, 10-80%, 10-75%, 10-60%, 10-50%, 10-40%, 10-35%, 10-30%, 10-25%, 10-20%, 10-15%, 20-80%, 20-75%, 20-60%, 20-50%, 20-40%, 20-35%, 20-30%, 20-25%, 20-15%, 30-80%, 30-75%, 30-60%, 30-50%, 30-40%, 30-35%, 35-80%, 35-75%, 35-60%, 35-50%, 35-40%, 40-80%, 40-75%, 40-60%, 40-50%, 50-80%, 50-75%, 50-60%, 60-80%, 60-75%, or 75-80% of the non-aqueous solvent. In specific, non-limiting embodiments, the solvent mixture comprises about 5%, about 10%, about 15%, about 20%, about 25%, about 30%, about 35%, about 40%, about 45%, about 50%, about 60%, about 70%, about 75%, about 80%, about 90%, or about 95% of the non-aqueous solvent. Particular, but non-limiting embodiments, include the organic solvent and water in a ratio of about 10:90 to about 90:10.

In one embodiment, the casting solution is formed by dissolving or suspending both the at least one agent and the one or more polymers in the solvent to form a solution or suspension comprising the active agent and the polymer. In another embodiment, the at least one active agent is dissolved or suspended in a first solvent to form an active agent solution or suspension. The at least one polymer is separately dissolved in a solvent to form a polymer solution or suspension. The suspension may be a liquid in liquid suspension or a solid in liquid suspension depending on the nature of the active agent and/or polymer. The solvent used for the active agent solution and the polymer solution may be the same or different. The active agent solution and the polymer solution are mixed to form a polymer matrix solution or suspension. It will further be appreciated that a solvent mixture may be used to dissolve or suspend the active agent and/or polymer.

One or more excipients may be dissolved or suspended in the casting solution or formulation. Suitable excipients include, but are not limited to, one or more stabilizers, plasticizers, surfactants, and/or anti-oxidants. In one embodiment, a solubility enhancer is included in the casting solution or formulation. The solubility enhancer may (i) enhance the solubility of the agent and/or polymer in the solvent, and/or (ii) enhance the solubility of the agent after delivery. It will be appreciated that the solubility enhancer may have the effect of both (i) and (ii).

One or more surfactants may be added to the casting solution. Surfactants may be added to change the solutions' surface tension and/or reduce the hydrophobic interactions of proteins. Any suitable surfactant as known in the art may be used. Exemplary surfactants include, but are not limited to, emulsifiers such as Polysorbate 20 and Polysorbate 80.

One or more antioxidants may be added to the casting solution. Any suitable antioxidant as known in the art may be used. Exemplary antioxidants include, but are not limited to, methionine, cysteine, D-alpha tocopherol acetate, EDTA, and vitamin E.

Some exemplary casting solution formulations are described in Table 1 in Example 1 and Table 2 in Example 2.

The casting solution is dispensed on the mold or into the mold cavities. Where the solution is cast on the mold, the solution is moved into the cavities by any suitable means. In one embodiment, the mold surface with solution thereon is covered to spread the solution or formulation on the mold and at least partially into the cavities. In other embodiments, the solution is spread on the mold without covering. The cavities are filled with the casting solution. In one embodiment, the mold is pressurized, with or without a cover, to move the solution into or further into the cavities of the mold. Pressurization may be accomplished by placing the mold with the casting solution into a pressure vessel as known in the art. Pressurization may involve a pressure of at least about 3 psi, about 5 psi, about 10 psi, about 14.7 psi, about 20 psi, or about 50 psi above atmospheric. In other embodiments, pressurization involves a pressure of at least about 3-50 psi above atmospheric. In other embodiments, pressurization involves a pressure of at least about 3-40 psi, about 3-30 psi, about 3-20 psi, about 3-14.7 psi, about 3-10 psi, about 3-5 psi, about 5-50 psi, about 5-30 psi, about 5-20 psi, about 5-14.7 psi, about 5-10 psi, about 10-50 psi, about 10-30 psi, about 10-20 psi, about 10-14.7 psi, about 20-50 psi, about 20-30 psi, or about 30-40 psi above atmospheric. Excess solution may be wiped or otherwise removed from the mold surface. In another embodiment, a soluble gas is used to move the casting solution into or further into the cavities. Specific, but not limiting, soluble gases are $CO_2$ and $CH_4$.

The mold may be treated prior to dispensing the casting solution to improve dispensing of the casting solution and/or to avoid or reduce the presence of air bubbles. In embodiments, the mold, or portions thereof, is treated to improve the ability of the casting solution to wet the mold. Suitable treatments are known in the art and described, for example, in U.S. Patent Publication No. 2008/0269685, which is incorporated herein in its entirety. In addition, or separately, the casting solution may include ingredients to prevent, reduce, or minimize bubbling. One exemplary ingredient is an anti-foaming agent. Another embodiment of a surface treatment includes coating at a least a portion of the mold with a substance that improves the ability of the casting solution or suspension to wet the mold surface. In non-limiting embodiments, at least a portion of the mold surface is coated with at least one of calcium carbonate, ethyl acetate, a silicone fluid, or oxygen plasma.

The solvent is removed from the mold. In one embodiment, the mold with liquid casting solution is dried using one or multiple primary drying steps based on physiochemical properties of the formulations including, but not limited to, viscosity, solid content, surface interaction between the formulation and the mold, etc. Drying causes volume change in the formulation and hence the movement of the formulation down to the distal end of the mold cavity. Surface drying causes the formulation to "pin" to the walls of the mold cavity thereby arresting the downward movement of the formulation. Multiple primary drying steps may be useful where pinning would occur early in the drying process. Exemplary methods of drying are described in U.S. Patent Publication No. 2014/0272101, which is incorporated herein by reference.

In non-limiting embodiments, the mold with liquid casting solution may be dried using a one-step or two-step primary drying method to remove the solvent. In one embodiment, the mold with the liquid casting solution is dried using a one-step primary drying step. In this embodiment, the mold with liquid casting solution is dried at a temperature of about 25-50° C., e.g. 32° C., for about 20 minutes to two or three hours. In another embodiment, the mold with liquid casting solution is dried using a two-step primary drying method. In this embodiment, the mold with liquid casting solution is first dried at a temperature of about 5-50° C., e.g. 32° C., for a period of time. This first primary drying step is usually about 1-30 minutes. This initial primary drying step may involve controlled humidity and/or controlled partial pressure. In embodiments, the humidity in the chamber is controlled from at least about 10% to about 95% relative humidity (RH). In other embodiments, the partial pressure in the chamber is controlled from about 0.01 mTorr to about 230 Torr. The air convection in the chamber may also be controlled with no convection, low air convection, or high convection. The mold with liquid casting solution is then further dried at a temperature of about 5-50° C. for about 30 minutes to several hours (e.g. two hours).

In an embodiment, the mold is dried from below as described in U.S. Patent Publication No. 2014/0272101, which is incorporated herein by reference. In this embodiment, the mold is dried from beneath, under or below the mold. It will be appreciated that the casting solution may be dried from substantially beneath, under or below the mold. Under drying has the benefit of even microstructure formation and/or low meniscus of the microstructures. In addition, the under method of drying has the additional benefit of reducing time necessary for drying. In embodiments, the microstructure formulation is dried from underneath for 5-30 minutes. In other embodiments, the formulation is dried from underneath for 5-25 minutes, 5-20 minutes, 5-15 minutes, 5-10 minutes, 10-25 minutes, 10-20 minutes, 10-15 minutes, 15-25 minutes, 15-20 minutes, or 20-25 minutes. In specific embodiments, the formulation is dried from underneath for about 5, 10, 15, 20, 25, or 30 minutes. In embodiments, the mold is heated to maintain or substantially maintain the temperature of the formulation at about 5-50° C. The formulation may be dried from below using conductive and/or radiative heating. Under drying may also be used for drying the backing layer as described further below.

As shown in Table 3, the content of the active agent in the microstructure arrays formed by the present methods are very uniform, which indicates the formulations for use in preparing the microstructure arrays are physically stable. The active agent content in the microstructure arrays ranged from 180.0 µg to 186.4 µg with an average of 182.4 µg. The relative standard deviation (RSD) for the active agent content for three batches of formulation was extremely low and ranged from 1.4% to 3.0%. The RSD for all of the batches was only 1.6%. This demonstrates a high degree of uniformity in active agent content across the microstructure arrays prepared by the methods disclosed herein.

In one embodiment, an optional backing layer, base layer, or basement is further cast onto or otherwise added to the microstructures. Microstructure arrays typically use a polymer backing layer. A casting solution or formulation is prepared and dispensed on the mold or into the cavities. When the backing layer casting solution is dried or the solvent removed, the backing layer forms a continuous layer or structure with the drug/polymer matrix. The polymers typically used for preparing backing layers are usually soluble in organic or non-aqueous solvents. However, the problem arises when forming microstructure arrays to deliver poorly soluble therapeutic agents that are soluble in organic or non-aqueous solvents. When the casting solution comprising the polymer for the backing layer is dispensed on the microstructures in the mold, the poorly soluble agent may be extracted into the backing layer.

In one embodiment, the therapeutic agent should not be soluble or appreciably soluble in the solvent or solvent mixture used for the backing layer casting solution or formulation. With this in mind, in one embodiment, a liquid backing casting solution or formulation is formed by dissolving one or more suitable polymers in a solvent or solvent mixture. The therapeutic agent and/or polymers of the polymer solution or suspension are not soluble or not appreciably soluble in the solvent or solvent mixture used for the backing casting solution or formulation. In further embodiments, polymer solution or suspension does not mix or does not appreciably mix with the backing layer solution or suspension. In another non-limiting embodiment, less than about 1-50% of the active agent of the polymer solution or suspension dissolves, moves into, or is present in the backing polymer solution or suspension. In specific embodiments, less than about 1%, 5%, 10%, 15%, 20%, 25%, 30%, 40%, or 50% of the active agent dissolves, moves into, or is present in the backing polymer solution or suspension. The liquid backing formulation is dispensed on the mold or into the cavities. Some suitable polymers are described in U.S. Pat. No. 7,785,301, which is incorporated herein in its entirety. Liquid backing formulations may be moved into the cavities by the same or similar methods as for the active agent casting solution. Where a liquid backing layer formulation is used, the solvent of the backing layer formulation is removed by a drying process. The drying conditions for drying the backing layer should be controlled so that the backing layer solvent can be removed effectively without affecting the stability of an active agent and/or to properly form (e.g. uniform) the backing layer. Exemplary drying methods are described in U.S. Publication No. 2014/0272101 and 2008/0269685, each of which are incorporated herein by reference. In one embodiment, the mold is dried at about 5-50° C. for about 0-120 minutes. In one embodiment, the mold may be placed into a suitable oven for drying. In another embodiment, the mold is placed in a compressed dry air (CDA) box under controlled air flow and then placed in an oven at about 5-50° C. In further embodiments, the mold is placed in the oven at a temperature of about 5-50° C. In embodiments, the temperature of the CDA and/or oven is about 5° C., about 10° C., about 20° C., about 30° C., about 40° C., about 45° C., or about 50° C. In embodiments, the temperature of the CDA and/or oven is about 5-45° C., 5-40° C., 5-30° C., 5-20° C., 5-15° C., 5-10° C., 10-50° C., 10-45° C., 10-40° C., 10-30° C., 10-20° C., 10-15° C., 15-50° C., 15-45° C., 15-40° C., 15-30° C., 15-20° C., 20-50° C., 20-45° C., 20-40° C., 20-30° C., 30-50° C., 30-45° C., 30-40° C., 30-45° C., 40-50° C., 40-45° C., or 45-50° C. In embodiments, the oven uses convection, conduction, or radiation for drying. In another embodiment, the mold is placed in an oven at about 5-50° C. without prior time in a CDA box. In embodiments, the mold is placed in the CDA and/or oven for at least about 0-120 minutes, about 30-120 minutes, about 30-90 minutes, about 30-60 minutes, about 30-45 minutes, about 45-120 minutes, about 45-90 minutes, about 45-60 minutes, about 60-120 minutes, about 60-90 minutes, about 90-120 minutes, or longer. Residual solvents in the backing layer can be measured to determine the effectiveness of solvent removal under different drying conditions.

In another embodiment, the backing layer is an adhesive or other layer that is pre-formed and applied to the microstructures. The pre-formed layer is not cast using a solvent so the therapeutic agent is not extracted into the backing layer upon administration to the microstructures. In further embodiments, the backing layer is a non-solvent based liquid adhesive. These adhesives will be cured rather than requiring removal of solvent. Suitable adhesives include, but are not limited to the Dymax® UV-curable 1128A-M, 1161-M, 1162-M, 1165-M, 1180-M, and 1187-M medical device adhesives. It will be appreciated that any biocompatible adhesive is suitable for use with, in and/or as the backing layer. It will further be appreciated that selection of the adhesive may be based, at least in part, on the polymer used for the DIT portion of the MSA to ensure the adhesive is compatible with the DIT polymer(s). This layer may also be a nonwoven or porous film double coated with pressure sensitive adhesive.

As seen in Example 5, the use of a backing layer that does not permit the active agent to leach into or be extracted into the backing layer allows the majority of the active agent to remain in the delivery portion of the microstructure arrays. In many typical microstructure arrays, only the proximal portion, distal end or distal tip delivers the active agent to the subject. For example, the MicroCor® platform (Corium International, Inc.) uses biodegradable polymers such as poly(lactide-co-glycolide) in forming the backing layer. However, many poorly soluble drugs are soluble or highly soluble in organic solvents, which are used for casting the polymer backing layer. As described in Example 5, microstructure arrays were formed using (i) a cast polymer solution or (ii) a UV curable adhesive. The cast polymer solution is prepared by dissolving or suspending a polymer in an organic solvent. In Example 5, poly(lactide-co-glycolide) (PLGA) was used as an exemplary polymer. The polymer solution was deposited on the mold and the solution was moved into the mold cavities (or otherwise spread to contact the DIT portions containing the poorly soluble active agents) to form a continuous layer across the mold. The drug used in Example 5, like many poorly soluble agents, is highly soluble in organic solvents and can be extracted from the DIT portion into the backing layer. PLGA is a copolymer comprising different ratios of lactic acid and glycolic acid monomers. PLGA is biodegradable over an extended period (at least about two months) depending on the monomer ratio. Thus, PLGA is insoluble in a biological environment within a short period of time. As delivery of active agents from MSA is typically on the order of minutes to hours, the portion of any active agents that are extracted into a PLGA backing layer will not be delivered to the subject.

For comparison, microstructure arrays were prepared using a UV curable adhesive in forming a backing layer (Example 5). Each of the MSAs contained 180 μg of a poorly soluble active agent in a DIT portion. The MSAs having a polymer backing or a UV curable adhesive backing were immersed in ethyl alcohol for about 5 minutes to extract the poorly soluble active agent. Both of the PLGA and the UV curable adhesive backing layers are insoluble in ethyl alcohol. However, the DIT portion formed using PVP as the polymer is soluble in ethyl alcohol. Therefore, only the active agent present in the DIT portion is released into the ethyl alcohol solvent.

As seen in Table 4, nearly 100% of the active agent from the MSA having a UV curable adhesive backing layer was retained in the DIT portion and was, therefore, available for delivery to the subject. Only 118 μg of the active agent was retained in the DIT portion of the MSA having a polymer backing layer. Thus, only about 65% of the active agent was available for delivery. The remaining portion (about 40% of the active agent) was found in the PLGA backing layer (data not shown). In contrast, 177 μg of the active agent was retained in the DIT portion of the MSA having a UV curable adhesive backing layer. Nearly all of the active agent was retained in the DIT portion with >98% of the active agent extracted from the MSA having a UV curable adhesive backing layer.

In non-limiting embodiments, at least about 70-100% of the active agent is retained in a distal tip, end or portion of the microstructure arrays. In further embodiments, at least about 70-80%, 70-85%, 70-90%, 70-95%, 70-99%, 75-80%, 75-85%, 75-90%, 75-95%, 75-99%, 75-100%, 80-85%, 80-90%, 80-95%, 80-99%, 80-100%, 90-95%, 90-99%, 90-100%, 95-99%, 95-100%, or 99-100% of the active agent is retained in a distal tip, end or portion of the microstructure arrays.

As further shown in Table 5, only 49% of the active agent was recovered during extraction of the MSAs having a PLGA backing layer. The MSAs with the UV curable adhesive backing layer had a high retention of the active agent in the DIT layer with 100% of the active agent being recovered from the DIT portion.

Figure 7:
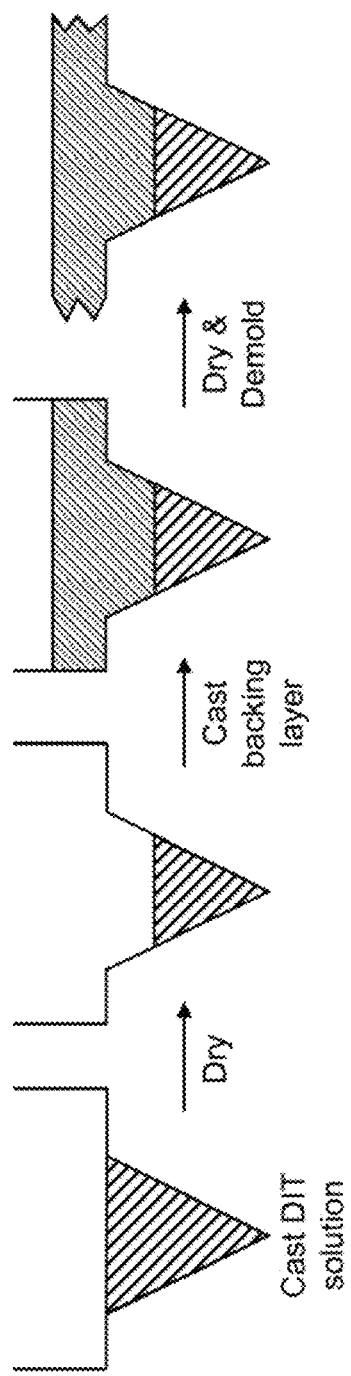
FIG. 7 is an illustration of an exemplary method of forming a microstructure array.

FIG. 7 is an illustration of exemplary methods of forming microstructures having a drug-in-tip (DIT) and a backing layer. As seen in FIG. 7, in one exemplary method, a liquid DIT solution is cast on a mold having at least one cavity in the shape desired for the microstructures. The liquid DIT is dried under controlled conditions to remove the solvent resulting in a solid DIT layer in the bottom or distal end of the cavity. In one embodiment, a backing layer is cast such that the remaining space in the cavity is filled and, optionally as shown in FIG. 7, a layer of backing layer formulation extends between the cavities. The backing layer is dried such that the resulting array has a backing layer with a plurality of microstructures extending at an angle from the backing layer. In another embodiment, a pre-formed backing layer is applied, adhered, or attached to the DIT layer. The backing layer with attached microstructures is demolded and may undergo an optional final drying step to form the microstructure array (MSA). It will be appreciated that the MSA may be demolded prior to undergoing the final drying step.

Example 4 describes an exemplary method of preparing a microstructure array including a UV curable backing layer. A liquid DIT solution is cast on a mold and the DIT formulation is moved into cavities in the mold. The DIT solution is dried. An adhesive is dispensed on the mold and cured using a UV curing system.

The MSAs formed by the methods herein are extremely stable. Stability as used herein refers to a microstructure array which retains a majority of the active agent during and after storage. As described in Example 6, the stability of exemplary MSAs was determined after storage for one or two weeks at low temperature or room temperature. As seen in Table 6, the MSAs retained a purity of 98.9% after storage at 4° C. for one week. MSAs further retained a purity of 98.5% after storage for two weeks. Thus, the MSAs are very stable after storage for at least one to two weeks at low temperatures and at room temperature. Further, the MSAs retained a purity of 98.9% after storage at 25° C. for one week. MSAs further retained a purity of 98.6% after storage for two weeks. Thus, the MSAs are also very stable after storage for about one to two weeks at low temperatures and at about room temperature. Purity and/or stability of the active agent in the MSA may be measured or determined by known methods including, but not limited to RP-HPLC, particle size, SDS-PAGE, SEC-HPLC and in vitro potency or SRID.

It is expected the MSAs will be stable after storage at low temperatures and/or at room temperature for one week to at least about one year or longer. In embodiments, the MSAs are stable after storage for at least about 1 week to 9 months, 1 week to 6 months, 1 week to four months, 1 week to three months, 1 week to two months, 1 week to one month, 1-3 weeks, 1-2 weeks, 2 weeks to one year, 2 weeks to 9 months, 2 weeks to 6 months, 2 weeks to four months, 2 weeks to three months, 2 weeks to two months, 2 weeks to one month, 2-3 weeks, 1-6 months, 1-12 months, 2-12 months, 3-12 months, 4-12 months, 5-12 months, 6-12 months, 7-12 months, 8-12 months, 9-12 months, 10-12 months, 11-12 months. In other embodiments, the MSAs are stable after storage for at least about 1 week, 2 weeks, 3 weeks, 1 month, 2 months, 3 months, 4 months, 5 months, 6 months, 7 months, 8 months, 9 months, 10 months, 11 months, 12 months, 18 months, 24 months, or more.

In some embodiments, stability of the MSA is based on maintaining a percentage of the active agent in the MSAs. In non-limiting embodiments, the MSAs retain at least about 50-100%, 60-100%, 70-100%, 75-100%, 80-100%, 90-100%, 95-100%, 99-100%, 50-99%, 50-95%, 50-90%, 50-80%, 50-75%, 50-70%, 50-60%, 60-99%, 60-95%, 60-90%, 60-80%, 60-75%, 60-70%, 70-99%, 70-95%, 70-90%, 70-80%, 70-75%, 75-99%, 75-95%, 75-90%, 75-80%, 75-75%, 75-70%, 80-99%, 80-95%, 80-90%, 90-99%, 90-95%, 95-99% of the active agent after storage. In specific, but not limiting embodiments, at least about 75%, 80%, 85%, 90%, 95%, 96%, 97%, 98%, 99%, or 100% of the active agent is retained in the MSA after storage.

The microprojections may further be positioned on a base or substrate to form the array. The substrate may be in addition to a backing layer. In another embodiment, the substrate is the backing layer. The microprojections may be attached to the substrate by any suitable means. In one, non-limiting embodiment, the microstructures are attached to the substrate using an adhesive. Suitable adhesives include, but are not limited to, acrylic adhesives, acrylate adhesives, pressure sensitive adhesives, double-sided adhesive tape, double sided adhesive coated nonwoven or porous film, and UV curable adhesives. One exemplary double-sided tape is the #1513 double-coated medical tape available from 3M. One exemplary, but non-limiting, UV curable adhesive is the 1187-M UV light-curable adhesive available from Dymax. It will be appreciated that any medical device adhesive known in the art would be suitable. In one embodiment, the substrate is a breathable nonwoven pressure sensitive adhesive. The substrate is placed on the backing layer where present or a proximal surface of the microprojections. The substrate is adhered or attached to the microprojections. In another embodiment, the substrate is a UV cured adhesive in a polycarbonate film. The UV adhesive is dispensed on the top of the backing layer or the proximal surface of the microprojections, covered with a polycarbonate (PC) film to spread the adhesive and cured using a UV Fusion system. In one embodiment a UV curing dose is about 1.6 J/cm². After the substrate is attached or adhered to the microprojections, the microprojection array is removed from the mold. It will be appreciated where the array includes a backing layer the substrate is attached or adhered to the backing layer as described above for the microstructures.

Cast microprojection arrays are removed from the mold by any suitable means. In one embodiment, the microprojection array is removed from the mold by using a de-mold tool which has a rolling angle of about 1-90 degrees from the plane. A double-sided adhesive is placed on the back of microprojection array with one side for adhering to the array and the other side for adhering to the de-mold tool. The array is removed from the mold by gently rolling the de-mold tool over the adhesive on the back of the array with a slight the rolling angle, such as about 1-90 degrees, preferred about 5-75 degrees, more preferred about 10-45 degrees. The microprojection array is then gently peeled off from the de-mold tool. The arrays may be demolded after drying the backing layer or after a final drying step.

Before or after the microprojection array is removed from the mold a final drying step may be performed under vacuum. The final drying may be at room temperature or at an elevated temperature. In embodiments, the final drying is at about 5-50° C. In embodiments, the final drying is at about 5° C., at about 10° C., at about 20° C., at about 25° C., at about 35° C., at about 40° C., at about 45° C., or at about 50° C. Further suitable temperatures and ranges are described above with reference to drying the backing layer. In embodiments, the final drying is from about 1-24 hours or longer, from about 4-20 hours, from about 6-10 hours, from about 8-16 hours, from about 8-12 hours, from about 8-10 hours, from about 10-12 hours, from about 10-16 hours, from about 12-16 hours or longer. In other embodiments, the final drying step is overnight.

After the microprojection array is removed from the mold, it may be cut to an appropriate size and/or shape. In one embodiment, the microprojection array is die cut with an 11 or 16 mm punch.

Figure 1B:
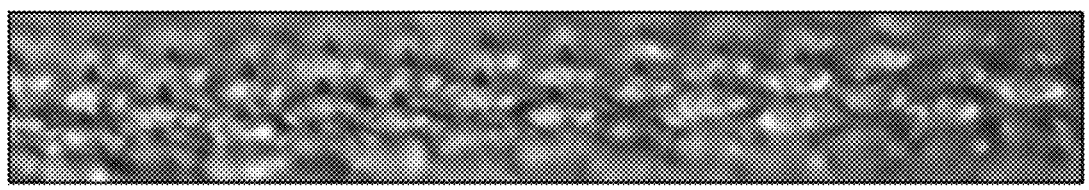

The disclosed methods of forming microprojection arrays result in microstructures that dissolve evenly. As described in Example 7, microstructure arrays were formed and immersed in rat serum for five minutes to mimic insertion of the microprojections in a biological environment. As seen in FIG. 1B, the stumps of the projections quickly and evenly dissolved.

IV. METHODS OF USE

The methods, kits, microstructure arrays and related devices described herein may be used for treating any condition. It will be appreciated that the microstructure arrays may be used with any appropriate applicator including the applicators described in U.S. Publication No. 2011/0276027 as well as those described in U.S. Provisional application Nos. 61/778,274 and 61/801,904 (published as US 2014/0276580 and US 2014/0276366, respectively), each of which are incorporated herein in their entirety.

V. EXAMPLES

The following examples are illustrative in nature and are in no way intended to be limiting. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

Formulating a Microstructure Casting Formulation with a Poorly Soluble Agent

Liquid casting formulations are prepared using an active pharmaceutical ingredient (API), hetastarch as a polymer (hydroxyethyl starch, molar substitution approximately 0.75 (i.e., approximately 75 hydroxyethyl groups per 100 glucose units)), a surfactant and/or a solubility enhancer in an organic solvent/water mixture as shown in Table 1. In these formulations, VitE TPGS or Kolliphor is used as a solubility enhancer. The API has a solubility in water of about 0.03 mg/mL

TABLE 1

Liquid Casting Solution Formulations using Hetastarch as the Polymer

| Hetastarch | VitE TPGS | Kolliphor | Active Agent | ETOH (% in solvent) |
|---|---|---|---|---|
| 15.00% | 3.0% | 0% | 1.5% | 35.0% |
| 15.00% | 0% | 3.0% | 1.5% | 35.0% |
| 15.00% | 0% | 3.0% | 1.5% | 40.0% |
| 15.00% | 3.00% | 0% | 1.5% | 40.0% |
| 15.00% | 5.00% | 0% | 1.5% | 40.0% |
| 15.00% | 5.00% | 0% | 2.0% | 40.0% |
| 15.00% | 5.00% | 0% | 2.0% | 50.0% |
| 15.00% | 3.00% | 0% | 2.0% | 50.0% |
| 15.00% | 0% | 5.0% | 2.0% | 50.0% |

To prepare the liquid casting formulation, hetastarch is dissolved in water to form the polymer stock solution. The active agent and solubility enhancer (VitE TPGS or Kolliphor) are separately dissolved in ethyl alcohol to form the active agent and enhancer stock solutions, respectively. The enhancer stock solution and active agent stock solution are sequentially added to the polymer stock solution.

Example 2

Formulating a Microstructure Casting Formulation with a Poorly Soluble Agent

Liquid casting formulations are prepared using an active pharmaceutical ingredient (API) that is poorly water soluble, PVP as a polymer, glycerol (plasticizer), and Kolliphor ELP (solubility enhancer) in an organic solvent/water mixture as shown in Table 2. The API has a solubility in water of about 0.03 mg/mL

TABLE 2

Liquid Casting Solution Formulations using PVP as the Polymer

| PVP (wt %) | Glycerol (wt %) | Kolliphor ELP (wt %) | Active Agent (wt %) |
|---|---|---|---|
| 21 | 1.1 | 0 | 10 |
| 25 | 0.0 | 0 | 17 |
| 30 | 1.5 | 0 | 10 |
| 30 | 0.0 | 1 | 10 |
| 30 | 0.0 | 3 | 8 |
| 30 | 0.0 | 5 | 8 |
| 30 | 0.0 | 5 | 10 |
| 30 | 1.5 | 5 | 10 |
| 30 | 0.0 | 0 | 10 |
| 30 | 1.5 | 0 | 10 |
| 35 | 1.5 | 0 | 10 |
| 30 | 0.0 | 0 | 14 |
| 30 | 1.5 | 0 | 14 |
| 30 | 0.0 | 0 | 18 |

To prepare the liquid casting formulation, stock solutions of PVP, glycerol and the active agent are prepared using ethyl alcohol as a solvent. The glycerol, Kolliphor ELP, and active agent stock solutions are sequentially added to the polymer stock solution to form a single phase formulation.

Example 3

Casting Microstructure Arrays

Liquid casting formulations are prepared according to Example 2. About 90 µL of liquid casting solution formulation is dispensed on a silicone mold. The formulation is wiped and then dried to form the microstructures. Alternatively, about 75 µl of liquid formulation is cast into a silicone mold, covered with 22×30 mm glass cover slip, pressurized at 50 psi for 1 min, wiped, and dried.

After wiping, the liquid formulation contained in the mold is dried in either one or two primary drying steps, depending, for example, on the physicochemical properties of the respective liquid formulations, such as viscosity, solids content, surface interaction between liquid formulation and mold, etc. In one-step primary drying, the liquid formulation contained in the mold is directly placed in an incubator oven at about 5-50° C., typically about 32° C., for about 30 min to remove the solvent. When two-step drying was conducted, the first step is a slow drying step in which the liquid formulation-filled mold is first placed in a small chamber where the atmosphere is filled with the solvent of the liquid casting formulation for 1-30 min at a temperature of about 5-50° C., typically at room temperature. The mold is then placed in an incubator oven at about 5-50° C., typically about 32° C. for about 30 min.

Example 4

Casting Microstructure Arrays with Backing Layer

Microstructures formed according to Example 3 are prepared. A UV curable adhesive is dispensed onto the mold. The UV curable adhesive is cured using a UV Fusion system. The UV curing dose is 1.6 J/cm². The time for curing the UV curable adhesive may be 0.1 seconds or greater. The microstructure array is then demolded.

The arrays are very well formed with straight and sharp microstructures as shown in FIG. 1A.

The microstructure arrays are uniform as shown in Table 3, which indicates the microstructure formulations are physically stable.

TABLE 3

Microstructure uniformity

| Batch # | Average active agent content (µg) | RSD | Average (µg) | RSD |
|---|---|---|---|---|
| 1 | 180.0 | 1.8% | 182.4 | 1.6% |
| 2 | 180.3 | 1.4% | | |
| 3 | 186.4 | 2.5% | | |
| 4 | 183.1 | 3.0% | | |

Example 5

Extraction of Active Agent from Arrays

Microstructure arrays prepared in accord with Example 4 are compared with microstructure arrays prepared using a polymer backing layer.

Microstructure arrays using a polymer backing layer are prepared by preparing microstructures in accord with Example 2. A backing layer polymer solution comprising poly(lactide-co-glycolide) (PLGA) in an organic solvent is prepared and dispensed on the mold. A thin film is cast by wiping the backing layer solution. The mold is dried. Each of the microstructure arrays having a UV curable backing layer or a polymer backing layer have an active agent load of 180 µg/array.

The microstructure arrays with the UV curable backing layer and the polymer backing layer are extracted with ethyl alcohol. The PVP microstructure is soluble in ethyl alcohol and will release contained drug upon extraction. Neither the UV curable backing layer nor the polymer backing layer is soluble in ethyl alcohol. Active agents contained in these backing layers will be difficult to extract with ethyl alcohol. Therefore, any drug recovered by extraction is from the PVP microstructure. The arrays are immersed in ethyl alcohol for 5 minutes with the results shown in Table 5.

TABLE 4

Dissolution of active agent from microstructure

| Backing layer material | Active agent in PVP microstructure (µg) | Fraction of active agent in PVP microstructure |
|---|---|---|
| UV curable adhesive | 177 | 98% |
| PLGA | 118 | 66% |

TABLE 5

Active agent recovery during extraction

| Backing layer | Recovery | RSD |
|---|---|---|
| PLGA | 49% | 14% |
| UV-curable adhesive | 101% | 2% |

Example 6

Stability of Arrays

Figure 3:
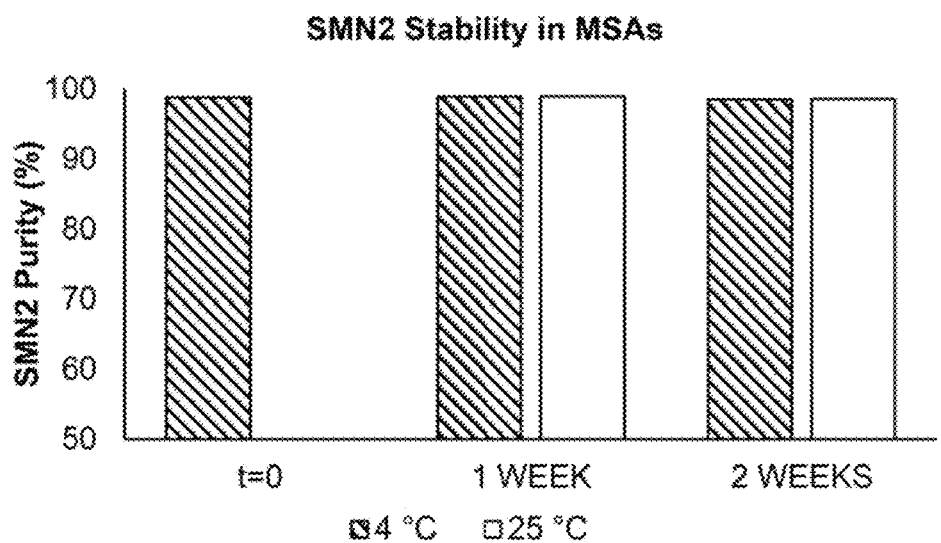
FIG. 3 shows the stability of microstructure arrays prepared by an embodiment of the present method.

Microstructure arrays are prepared in accord with Example 4. The liquid casting formulations is prepared with about 30% PVP, about 1.5% Glycerol, and about 10% of a poorly soluble active agent in EtOH. The solid content of the formulation is about 41.5% of the formulation. The percentage of active agent in the solids is about 24%. To determine shelf-life stability, microstructures prepared with an active agent were sealed in polyfoil pouches and stored at 4° C. or 25° C. for one or two weeks, which was the duration of the studies. RP-HPLC is used to characterize the stability of the active agents employed. The content and purity of the active agent in the microstructures was measured after storage with the results shown in Table 6. FIG. 3 is a plot of the active agent purity at t=0 and after storage for one or two weeks at 4° C. or 25° C., respectively.

TABLE 6

Stability of Active Agent After Storage

| Storage Time (weeks) | Storage Temperature (° C.) | Active Content (µg/cm) | Active Content Average (µg/cm) | RSD | Purity Average % | RSD |
|---|---|---|---|---|---|---|
| 0 | | 181.0 | 186.4 | 2.51% | 98.8 | 0.23% |
| 0 | | 184.4 | | | | |
| 0 | | 191.8 | | | | |
| 0 | | 188.3 | | | | |
| 1 | 4 | 184.2 | 189.8 | 5.09% | 98.9 | 0.08% |
| 1 | 4 | 184.3 | | | | |
| 1 | 4 | 201.0 | | | | |
| 1 | 25 | 200.1 | 209.9 | 9.31% | 98.9 | 0.05% |
| 1 | 25 | 197.2 | | | | |
| 1 | 25 | 232.4 | | | | |
| 2 | 4 | 178.2 | 174.1 | 2.14% | 98.5 | 0.07% |
| 2 | 4 | 171.0 | | | | |
| 2 | 4 | 173.1 | | | | |
| 2 | 25 | 186.7 | 198.5 | 15.17% | 98.6 | 0.03% |
| 2 | 25 | 232.8 | | | | |
| 2 | 25 | 176.1 | | | | |

The microstructure arrays were stable at 4° C. or 25° C. for at least 1-2 weeks, the duration studied. Based upon these and the additional data described below, active agent containing microstructure arrays comprising formulations as provided herein possess good mechanical performance, good active agent stability, as well as good performance based upon therapeutic response.

Example 7

Dissolution of Arrays

Microstructure arrays prepared in accord with Example 4 were immersed in rat serum for five minutes, which was used to mimic a biological environment. FIG. 1B shows a microstructure array after dissolution.

Example 8

In Vitro Skin Penetration Efficiency

Experiments are performed to assess the mechanical strength and penetration efficiency of the microstructure arrays formulated as described in Example 4. In vitro performance is characterized by the microstructure array's ability to penetrate excised pig skin.

Full-thickness pig skin is excised from the abdomen and then clipped and shaved to remove hair bristles. Microstructure arrays are applied to shaved skin sites using a reusable application and held by hand in situ for about 5 to 15 minutes. Application sites are stained and photographed to visualize the microstructure penetrations. Penetrations are quantified using a custom developed image analysis program. Skin penetration efficiency (SPE) is then calculated based on the theoretical number of microstructures expected for the constructed microstructure array as follows:

% SPE=100×(no. penetrations/no. microstructures)

Figure 2:
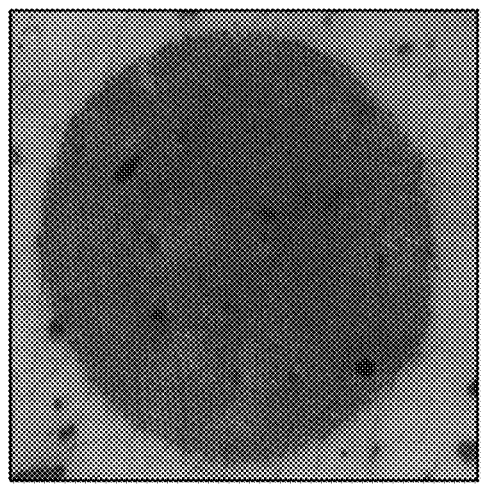
FIG. 2 is an image showing skin penetration by an exemplary microprojection array.

FIG. 2 is an image of the application site. The skin penetration efficiency was over 95%.

1. A microstructure apparatus comprising:
a backing having a first surface and a second surface opposed thereto;
a microstructure array comprising a plurality of microstructures extending outwardly from the first surface of the backing;
each of the plurality of microstructures comprising a biodegradable and/or bioerodible, water soluble distal layer;
wherein the distal layer comprises (i) at least one therapeutic agent that is poorly soluble in water or an aqueous solvent, and (ii) one or more polymers, the polymers being selected from polymers that (a) are soluble in an aqueous solvent and are soluble in an organic solvent, or (b) are soluble in an organic solvent/aqueous solvent mixture.

2. The apparatus of embodiment 1, the distal layer further comprising:
at least one solubility enhancer.

3. The apparatus of the combined or separate embodiments 1-2, wherein the at least one polymer is soluble in water or an aqueous solvent and the at least one polymer further includes hydrophilic properties.

4. The apparatus of the combined or separate embodiments 1-3, wherein the at least one polymer is selected from a starch derivative, polysaccharide, polyvinyl alcohol (PVA), and polyvinyl pyrrolidone (PVP).

5. The apparatus of the combined or separate embodiments 1-4, wherein the starch derivative is hetastarch.

6. The apparatus of the combined or separate embodiments 1-5, wherein the polysaccharide is dextran.

7. The apparatus of the combined or separate embodiments 1-6, wherein the at least one solubility enhancer is selected from an emulsifier and a solubilizer.

8. The apparatus of the combined or separate embodiments 1-7, wherein the at least one solubility enhancer is selected from D-α tocopheryl polyethylene glycol 1000 succinate and Kolliphor.

9. The apparatus of the combined or separate embodiments 1-8, wherein the backing is a UV-curable adhesive.

10. The apparatus of the combined or separate embodiments 1-9, wherein the therapeutic agent has a solubility in water or an aqueous solvent of less than about 10 mg/mL to about 1 mg/mL.

11. The apparatus of the combined or separate embodiments 1-10, wherein the therapeutic agent has a solubility in water or an aqueous solvent of less than about 1 mg/mL to about 100 µg/mL.

12. The apparatus of the combined or separate embodiments 1-11, wherein the therapeutic agent has a solubility in water or an aqueous solvent of less than about 100 µg/mL.

13. The apparatus of the combined or separate embodiments 1-12, wherein the therapeutic agent has a solubility in water or an aqueous solvent of less than about 50 µg/mL.

14. The apparatus of the combined or separate embodiments 1-13, wherein the therapeutic agent has a solubility in water or an aqueous solvent of less than about 30 µg/mL.

15. The apparatus of the combined or separate embodiments 1-14, wherein the therapeutic agent has a solubility in water or an aqueous solvent of less than about 1 µg/mL.

16. The apparatus of the combined or separate embodiments 1-15, further comprising:
a substrate having a first surface and a second surface opposed thereto, wherein the second surface of the backing is affixed to the first surface of the substrate.

17. A method for making a microstructure array comprising:
(a) mixing (i) a therapeutic agent that is poorly soluble in an aqueous solvent, and (ii) one or more polymers in (iii) a solvent selected from an organic solvent and an organic solvent/aqueous solution mixture to form a polymer solution or suspension;
(b) dispensing the polymer solution or suspension on a mold having an array of microstructure cavities;
(c) filling the microstructure cavities in the mold;
(d) removing excess solution or suspension on the mold surface; and
(e) drying the solution or suspension at about 5° C. to 50° C. to form an array of microstructures.

18. The method of embodiment 17, wherein drying the solution comprises drying the solution or suspension in a chamber having at least one of:
(i) a partial pressure of about 30 psi to 60 psi at a temperature of about 5° C. to 50° C.; or
(ii) an atmosphere filled with solvent of the liquid casting formulation at a temperature of about 5° C. to 50° C.

19. The method of the combined or separate embodiments 17-18 further comprising:
(f) drying the microstructure under vacuum at about 5° C. to 50° C.

20. The method of the combined or separate embodiments 17-19, wherein the chamber uses convection, conduction or radiation for drying.

21. The method of the combined or separate embodiments 17-20, further including a solubility enhancer in step (a).

22. The method of the combined or separate embodiments 17-21, further comprising:
(g) dissolving a polymer in a second organic solvent to form a backing polymer solution or suspension,
wherein neither of the therapeutic agent nor the one or more polymers of step (a) are appreciably soluble in the second organic solvent;
(h) dispensing a basement or backing layer on the mold surface; and
(i) drying the basement or backing layer.

23. The method of the combined or separate embodiments 17-22, further comprising:
(g) dissolving a polymer in a second organic solvent to form a backing polymer solution or suspension,
wherein the polymer solution or suspension and the backing polymer solution or suspension do not appreciably mix;
(h) dispensing a basement or backing layer on the mold surface; and
(i) drying the basement or backing layer.

24. The method of the combined or separate embodiments 17-23, wherein less than about 50% of the active agent is present in the backing polymer solution or suspension.

25. The method of the combined or separate embodiments 17-24, wherein less than about 40% of the active agent is present in the backing polymer solution or suspension.

26. The method of the combined or separate embodiments 17-24, wherein less than about 30% of the active agent is present in the backing polymer solution or suspension.

27. The method of the combined or separate embodiments 17-24, wherein less than about 20% of the active agent is present in the backing polymer solution or suspension.

28. The method of the combined or separate embodiments 17-24, wherein less than about 10% of the active agent is present in the backing polymer solution or suspension.

29. The method of the combined or separate embodiments 17-24, wherein less than about 5% of the active agent is present in the backing polymer solution or suspension.

30. The method of the combined or separate embodiments 17-29, wherein drying the basement or backing layer comprises drying in an oven at about 5° C. to 50° C.

31. The method of the combined or separate embodiments 17-30, further comprising affixing the basement or backing layer to a substrate.

32. The method of the combined or separate embodiments 17-31, further comprising attaching a UV curable adhesive backing layer to the microstructure array.

33. The method of the combined or separate embodiments 17-32, wherein the solvent is selected from ethanol, isopropyl alcohol, acetonitrile, DMSO, and NMP.

34. The method of the combined or separate embodiments 17-33, wherein the organic solvent/aqueous solution mixture is selected from ethanol:$H_2O$, and isopropyl alcohol:$H_2O$.

35. The method of the combined or separate embodiments 17-34, wherein the mixture comprises the organic solvent and $H_2O$ in a ratio of about 10:90 to about 90:10.

36. The method of the combined or separate embodiments 17-35, wherein the organic solvent/aqueous solution mixture is selected from DMSO:$H_2O$, and NMP:$H_2O$.

37. The method of the combined or separate embodiments 17-36, wherein the mixture comprises the DMSO and $H_2O$ in a ratio of about 10:90 to about 90:10.

38. The method of the combined or separate embodiments 17-37, wherein the mixture comprises the NMP and $H_2O$ in a ratio of about 10:90 to about 90:10.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

What is claimed is:

1. A microstructure apparatus comprising:
a backing having a first surface and a second surface opposed thereto;
a microstructure array comprising a plurality of microstructures extending outwardly from the first surface of the backing;
each of the plurality of microstructures comprising a biodegradable and/or bioerodible, water soluble distal layer having a distal tip;
wherein the distal layer comprises
(i) at least one therapeutic agent that is poorly soluble in water or an aqueous solvent where the agent has a solubility of less than 10 mg/mL in water at 25° C., and where the at least one therapeutic agent is uniformly dispersed in the distal layer of the microstructures,
(ii) one or more water soluble polymers, the one or more water soluble polymers being selected from polymers that
(a) are soluble in an aqueous solvent and are soluble in an organic solvent, or
(b) are soluble in an organic solvent/aqueous solvent mixture; and
(iii) at least one solubility enhancer,
wherein each distal layer in the plurality of microstructures comprises the distal tip formed as a piercing element, said piercing element adapted to penetrate at least a portion of the stratum corneum or a biological membrane.

2. The apparatus of claim 1, wherein the one or more water soluble polymers has hydrophilic properties.

3. The apparatus of claim 1, wherein the one or more water soluble polymers comprises one selected from a starch derivative, a polysaccharide, polyvinyl alcohol (PVA), and polyvinyl pyrrolidone (PVP).

4. The apparatus of claim 3, wherein the starch derivative is hetastarch.

5. The apparatus of claim 3, wherein the polysaccharide is dextran.

6. The apparatus of claim 1, wherein the at least one solubility enhancer is selected from an emulsifier and a solubilizer.

7. The apparatus of claim 1, wherein the at least one solubility enhancer is selected from D-α tocopheryl polyethylene glycol 1000 succinate and polyethoxylated castor oil.

8. The apparatus of claim 1, wherein the backing is a UV-curable adhesive.

9. The apparatus of claim 1, wherein the therapeutic agent has a solubility in water at 25° C. of less than 10 mg/mL to 1 mg/mL.

10. The apparatus of claim 1, wherein the therapeutic agent has a solubility in water at 25° C. of less than 1 mg/mL to 100 μg/mL.

11. The apparatus of claim 1, wherein the therapeutic agent has a solubility in water at 25° C. selected from less than 100 μg/mL; less than 50 μg/mL; less than 30 μg/mL; or less than 1 μg/mL.

12. The apparatus of claim 1, further comprising:
a substrate having a first surface and a second surface opposed thereto, wherein the second surface of the backing is affixed to the first surface of the substrate.

* * * * *